(12) United States Patent
Wang et al.

(10) Patent No.: US 6,916,610 B2
(45) Date of Patent: Jul. 12, 2005

(54) METHOD FOR GENERATION OF LONGER CDNA FRAGMENTS FROM SAGE TAGS FOR GENE IDENTIFICATION

(75) Inventors: San Ming Wang, Chicago, IL (US); Jian-jun Chen, Chicago, IL (US); Janet D. Rowley, Chicago, IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 09/748,710

(22) Filed: Dec. 22, 2000

(65) Prior Publication Data

US 2003/0104369 A1 Jun. 5, 2003

Related U.S. Application Data

(60) Provisional application No. 60/174,391, filed on Jan. 3, 2000, and provisional application No. 60/173,617, filed on Dec. 29, 1999.

(51) Int. Cl.[7] .......................... C12Q 1/68; C12P 19/34; C07H 21/02; C07H 21/04
(52) U.S. Cl. ..................... 435/6; 435/91.2; 536/23.1; 536/24.3; 536/24.33
(58) Field of Search .................. 435/6, 91.2; 536/24.3, 536/23.1, 24.33

(56) References Cited

U.S. PATENT DOCUMENTS

| | | | |
|---|---|---|---|
| 5,866,330 A | 2/1999 | Kinzler et al. .................. | 435/6 |
| 6,461,814 B1 * | 10/2002 | Spinella .......................... | 435/6 |

FOREIGN PATENT DOCUMENTS

| | | |
|---|---|---|
| WO | WO 98/53319 | 11/1998 |
| WO | WO 00/18966 | 4/2000 |

OTHER PUBLICATIONS

Birch, "Targeted differential display of abundantly expressed sequences from the basidiomcete *Phanerochaete chrysosporium* which contain regions coding for fungal celulose–binding domains," *Curr. Genet.*, 33:70–76, 1998.

Chavi et al., "Survey and characterization of viruses in sweetpotato from Zimbabwe," *Plant Disease*, 81(10):1115–1122, 1997.

Angelastro et al., "Identification of diverse nerve growth factor–regulated genes by serial analysis of gene expression (SAGE) profiling," *Proc. Nat'l Acad Sci USA*, 97(19):10424–10429, 2000.

Charpentier et al., "Effects of estrogen on global gene expression: identification of novel targets of estrogen action," *Cancer Res.*, 60:5977–5983, 2000.

Chen et al., "Characterization of gene expression in resting and activated mast cells," *J. Exp. Med.*, 188(9):1657–1668, 1998.

Chen et al., "Generation of longer cDNA fragments from serial analysis of gene expression tags for gene identification," *Proc. Natl. Acad. Sci. USA.*, 97(1):349–353, 2000.

El–Meanawy et al., "Use of serial analysis of gene expression to generate kidney expression libraries," *Am. J. Physiol. Renal. Physiol.*, 279:F383–F392, 2000.

Hashimoto, et al., "Serial Analysis of Gene Expression in Human Monocyte–Derived Dendritic Cells," *Blood*, 94(3):845–852, 1999.

Hibi et al., "Serial Analysis of Gene Expression in Non–Small Cell Lung Cancer," *Cancer Res.*, 58:5690–5694, 1998.

Hough et al., "Large–Scale Serial Analysis of Gene Expression Reveals Genes Differentially Expressed in Ovarian Cancer," *Cancer Res.*, 60:6281–6287, 2000.

Khan et al., "Efficient double stranded sequencing of cDNA clones containing long poly(A) tails using anchored poly(dT) primers," *Nucleic Acids Res.*, 19(7):1715, 1991.

Kiriangkum et al., "A reliable method for amplifying cDNA using the anchored–polymerase chain reaction (A–PCR)," *Nucleic Acids Res.*, 20(14):3793–3794, 1992.

Lee et al., "Generation of high quality and quantity of tag/ditag for SAGE analysis," *Biotechniques*, 2001.

Lee et al., "The pattern of gene expression in human CD15+ myeloid progenitor cells," *Proc. Nat'l. Acad. Sci. USA*, 98(6):3340–3345, 2001.

Liang and Pardee, "Differential Display of Eukaryotic Messenger RNA by Means of the Polymerase Chain Reaction," *Science*, 257:967–971, 1992.

Liang et al., "Differential display using one–base anchored oligo–dT primers," *Nucleic Acids Res.* 22(25):5763–5764, 1994.

Lundberg et al., "High–fidelity amplification using a thermostable DNA polymerase isolated from *Pyrococcus furiosus*," *Gene*,108:1–6, 1991.

(Continued)

Primary Examiner—Kenneth R. Horlick
Assistant Examiner—Joyce Tung
(74) Attorney, Agent, or Firm—Marshall, Gerstein & Borun LLP

(57) ABSTRACT

Generation of longer cDNA fragments from SAGE tags for gene identification (GLGI) is disclosed. This method converts SAGE tags, which are about 10 base pairs in length, into their corresponding 3' cDNA fragments covering hundred bases. This added information provides for more accurate genome-wide analysis and overcomes the inherent deficiencies of SAGE. The generation of longer cDNA fragments from isolated and purified protein fragments for gene identification is also disclosed. This method converts a short amino acid sequence into extended versions of the DNA sequences encoding the protein/protein fragment and additional 3' end sequences of the gene encoding the protein. This additional sequence information allows gene identification from purified protein sequences. The invention also provides a high-throughput GLGI procedure for identifying genes corresponding to a set of unidentified SAGE tags.

20 Claims, 7 Drawing Sheets

OTHER PUBLICATIONS

Madden et al., "SAGE transcript profiles for p53–dependent growth regulation," *Oncogene*, 15:1079–1085, 1997.

Van der Berg et al., "Serial analysis of gene expression: rapid RT–PCR analysis of unknown SAGE tags," *Nucleic Acids Res.*, 27(17):e17, 1999.

Velculescu et al., "Analysis of human transcriptomes," *Nat Genet.* 23:387–8, 1999.

Velculescu et al., "Characterization of the Yeast Transcriptome," *Cell*, 88:243–251, 1997.

Velculescu et al., "Series Analysis of Gene Expression," *Science*, 270:484–487, 1995.

Virlon et al., "Serial microanalysis of renal transcriptomes," *Proc. Nat'l. Acad. Sci. USA*, 96(26):15286–15291, 1999.

Wang and Rowley, "A strategy for genome–wide gene analysis: Integrated procedure for gene identification," *Proc. Nat'l. Acad. Sci. USA*, 95:11909–11914, 1998.

Wang et al., "Screening poly(dA/dT)⁻cDNAs for gene identification," *Proc Natl Acad Sci USA.*, 97(8):4162–4167, 2000.

Welle et al., "High–abundance mRNAs in human muscle: comparison between young and old," *J. Appl. Physiol.*, 89:297–304, 2000.

Welle et al., "Inventory of high–abundance mRNAs in skeletal muscle of normal men," *Genome Res.*, 9:506–513, 1999.

Zhang et al., Gene Expression Profiles in Normal and Cancer Cells, *Science*, 276:1268–1272, 1997.

Liang and Pardee, "Differential display of eukaryotic messenger RNA by means of the polymerase chain reaction," *Science*, 257:967–971, 1992.

Trenkle et al., "Differential display probes for cDNA arrays," *BioTechniques*, 27:554–564, 1999.

\* cited by examiner

METHOD FOR GENERATION OF LONGER CDNA FRAGMENTS FROM SAGE TAGS FOR GENE IDENTIFICATION

The present application claims the priority of co-pending U.S. Provisional Patent Applications, Ser. No. 60/173,617, filed Dec. 29, 1999, and Ser. No. 60/174,391, filed Jan. 3, 2000, the entire disclosures of which are incorporated herein by reference without disclaimer.

BACKGROUND OF THE INVENTION

1. Field of the Invention

The present invention relates generally to the field of genome-wide gene analysis. More particularly, it concerns the development of a technique wherein longer sequences extended from SAGE tags are generated to analyze gene expression. Furthermore, it concerns the development of a technique wherein extended DNA sequences encoding parts of an isolated protein fragment are generated to identify genes encoding isolated proteins. The invention also provides a high-throughput method for identifying genes encoded by SAGE tags.

2. Description of Related Art

A particular biological event in a cell is largely controlled by the expression of multiple genes, both at the correct time and in a spatially appropriate manner. Monitoring the pattern of gene expression under various physiological and pathological conditions is a critical step in understanding these biological processes and for potential intervention. Because of the large number of genes expressed in higher eukaryotic genomes, powerful tools are needed to characterize the overall pattern of gene expression. The successful development of the SAGE technique (Serial Analysis of Gene Expression) is an important milestone in this regard (Velculescu et al., 1995). In the SAGE technique, a short sequence tag with 10 base nucleotides representing each expressed sequence is excised and the tags from different expressed sequences are ligated for sequencing analysis. This strategy provides maximal coverage of the expressed genes for gene identification at the whole genome level while keeping the sequencing analysis at a manageable scale. Application of the SAGE technique has provided valuable information in various biological systems (Zhang et al., 1997, Velculescu et al., 1997, Madden et al., 1997, Hibi et al., 1998, Hashimoto et al., 1999).

However, there are two problems when applying the SAGE tag sequence for gene identification. The first is that many SAGE tags identified have no match to known sequences in databases (Zhang et al., 1997, Velculescu et al., 1997). These tags may represent potentially novel genes. It is difficult, however, to use this tag information for further characterization of the corresponding genes because of their short length. The second problem is that many SAGE tag sequences have multiple matches with sequences in the databases. These matched sequences have no similarity to each other except that they share the same SAGE tag sequence. This feature makes it difficult to determine the correct sequence in a particular tissue corresponding to a SAGE tag among these matched sequences.

SUMMARY OF THE INVENTION

To overcome these problems, the present inventors developed a technique called the Generation of Longer cDNA fragments from SAGE Tags for Gene Identification (GLGI). The key features of this technique are the use of a sequence containing a SAGE tag as the sense primer, and the use of a single-base anchored oligo-dT as the antisense primer, and Pfu DNA polymerase for PCR amplification. By using this approach, a SAGE tag sequence can be converted immediately into a longer cDNA fragment containing up to several hundred bases from the SAGE tag to the 3' end of the corresponding cDNA. The development of the GLGI technique overcomes the two obstacles discussed above and should have wide application in SAGE-related techniques for global analysis of gene expression. The same principle can be applied to confirm the reality of genes predicted by bioinformatics tools.

Therefore, in one embodiment of the present invention, there is provided a method for characterizing a SAGE tag fragment comprising (a) obtaining a RNA sample from the same tissue type as used in generating said SAGE tag; (b) generating cDNA fragments that correspond to the SAGE tag from said RNA sample by performing a DNA amplification reaction wherein primers used comprise:

(i) a SAGE tag sequence as a sense primer; and
(ii) at least one single-base anchored oligo-dT primer as an antisense primer; and
(iii) analyzing said cDNA fragments. The RNA sample preferably is the RNA sample used to perform SAGE. The DNA amplification preferably comprises polymerase chain reaction, for example, using Pfu DNA polymerase. The $Mg^{2+}$ concentration preferably is 4 mM. The cDNA fragments generated are generally about 50 to 600 base pairs in length.

The method uses single-base anchored oligo-dT primers comprising a single-base anchored to the 3' end of the oligo-dT primer said base excluding dT, preferably comprising from 10 to 25 poly-dT residues, even more preferably 11 poly-dT residues. The sense primer may further comprise a BamHI recognition sequence at the 5' end. The SAGE tag may further comprise a NlaIII recognition sequence at the 5' end.

The method may further comprise cloning cDNA fragments, sequencing the clones to identify the cDNA fragment sequence, and comparing the cDNA sequence to sequences in existing DNA databases. Alternatively, the method may comprise hybridizing the cDNA fragments with known sequences. In a more specific embodiment, the method comprises performing a DNA amplification reaction using (a) a sense primer designed based on an existing exon sequence, (b) a single-base anchored oligo-dT primer as an antisense primer, and (c) cloning and sequencing the amplified DNA. Cloning may advantageously include cloning into an expression vector, including a promoter operable in prokaryotic or eukaryotic cells. The exon sequences may be predicted by bioinformatics tools. The amplified sequences may be aligned with genomic DNA sequences.

The tissue type may be colon, thymus, small intestine, heart, placenta, skeletal muscle, testes, bone marrow, trachea, spinal cord, liver, spleen, brain, lung, ovary, prostate, skin, cornea, retina, and breast.

The present invention also describes a method for identifying a gene comprising: a) obtaining an isolated protein; b) digesting said protein to obtain at least a first protein fragment; c) obtaining at least a first amino acid sequence from said first protein fragment; d) generating a first DNA fragment that encodes said first protein fragment; e) performing a DNA amplification reaction with cDNA obtained from the same tissue sample as the isolated protein wherein primers used comprise: (i) a sense primer comprising said first DNA; and (ii) at least one single-base anchored oligo-dT primer as an antisense primer; and f) analyzing said cDNA fragments.

In one embodiment of the method the steps c) through f) are repeated with other protein fragments generated by the digestion. For example, the steps c) through f) can be repeated with a second protein fragment, a third protein, a fourth protein fragment, or a fifth protein fragment to mention a few. In some specific embodiments, at least three amino acid sequences are obtained from the protein.

In some embodiments of the method digesting the protein is followed by a separation to obtain purified protein fragments. The digestion may comprise the use of proteases well known in the art such as trypsin, chymotrypsin, elastase, collagenase, leupeptin and endopeptidases. Other protein digesting enzymes may also be used. Separation of the digested protein fragments may be based on the size of the protein fragments.

In specific embodiment of the method the separation and purification may involve protein precipitation; chromatographic techniques such as HPLC, FPLC, ion exchange chromatography, molecular sieve chromatography; size separation methods such as gel electrophoresis. Other separation and purification methods known in the art may be used as well.

In addition the invention also provides methods for simultaneously characterizing a set of SAGE tag fragments comprising: a) obtaining a RNA sample; b) generating cDNA fragments using a 3' anchored oligo dT primer for first strand synthesis; c) digesting the cDNA generated in step b) with an enzyme; d) isolating 3' cDNA fragments of the digested cDNA; e) amplifying the 3'cDNA fragments of step d) by (i) ligating a SAGE linker to the 3'cDNA; (ii) mixing the 3' cDNA with a sense primer comprising the sequence of the SAGE linker, an antisense primer comprising the sequence of the primer used in step b) or a fragment thereof, and a polymerase enzyme under conditions suitable for amplification; f) purifying the amplified 3'cDNA fragments obtained in step e); g) performing a second amplification comprising generation of longer cDNA fragments from SAGE tags in a multi-well format by mixing said 3' cDNA fragments with a sense primer comprising a SAGE tag sequence and a restriction enzyme sequence, an antisense primer comprising the sequence of the primer used in step b) or a fragment thereof; and a polymerase enzyme under conditions suitable for amplification; and h) cloning and sequencing the products generated in step g).

The 3' anchored oligo dT primer for first strand synthesis can be further attached to an affinity label such as biotin. This allows for isolation of the cDNA or fragments thereof by an affinity-based isolating method using for example streptavidin to recognize and bind the biotin. However, as will be recognized by the skilled artisan, one is not restricted to the use of streptavidin and biotin and any affinity label system may be used, for example, any antigen and its corresponding antibody, etc.

The enzyme used to digest the cDNA generated in step c) can be a restriction enzyme for example NlaIII. In a preferred embodiment the polymerase enzyme used in steps e) and g) of the method is PLATINUM Taq which provides high specificity and increases yield of the final product.

The steps of cloning and sequencing are well known to the skilled artisan and generically comprise: a) precipitating and purifying the amplified products of step g) in the multi-well format; b) cloning the purified products into a vector, c) transforming competent bacteria with cloned products; d) screening for transformants; and e) sequencing DNA from transformants to identify the gene encoded by the SAGE tag. In specific embodiments, the positive transformants are screened by direct colony-PCR™ amplifications.

In preferred embodiments of this method more than one SAGE tags are simultaneously identified. The multiple identification provides fr high-throughput The high-throughput generation of longer SAGE tags for gene identification (GLGI) procedure has several important features, for example, (i) 3' cDNAs instead of full-length cDNAs are used as the templates for GLGI amplification. This prevents artificial amplification from non-specific annealing of sense primer. The 3' cDNAs can be amplified to provide sufficient templates for GLGI amplification; (ii) a single antisense primer (in one example the primer is: 5'-ACTATCTAGAGCGGCCGCTT-3' (SEQ ID NO: 12) (see also Example 3)) is used for all GLGI reactions instead of using combination of the five anchored oligo dT primers. The sequence of the antisense primer is located in 3' end of all the cDNA templates incorporated from anchored oligo dT primers used for the first strand cDNA synthesis. Use of a single primer also increases the efficiency of GLGI amplification significantly as any annealing of this primer with 3' end sequence results in extension during PCR. This feature is particularly useful to amplify the templates with low copies; (iii) Use of PLATINUM Taq polymerase instead of Pfu DNA polymerase increases the yield of final products, while maintaining high specificity; (iv) the GLGI amplified DNAs are directly precipitated and cloned into vector without gel purification, which further prevents loss of amplified products. The inventors contemplate that this is especially important for products with short sizes and for products generated from templates with low copies. Thus, the methods of this invention provide the ability for large-scale identification of expressed genes. Genes of any eukaryotic origin, including human genes may therefore be identified at an accelerated rate by the simple, efficient and low-cost methods set forth herein.

Using the standard convention, "a" or "an" is defined herein to mean one or more than one. Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A). In this process, first strand cDNA synthesized by oligo-dT is used for PCR. In the first cycle, the template with the SAGE tag binding site is annealed by the sense primer and extended to the end of the template. In the second cycle, extension only occurs from the anchored oligo-dT primer annealed and paired correctly at the beginning of poly-dA sequences. Exponential amplification only occurs for the template with the SAGE tag binding site. (FIG. 1B). GLGI results in the conversion of a 10 bases of SAGE tag to hundred bases of 3' cDNA fragment.

DESCRIPTION OF ILLUSTRATIVE EMBODIMENTS

A. The Present Invention

Figure 1:
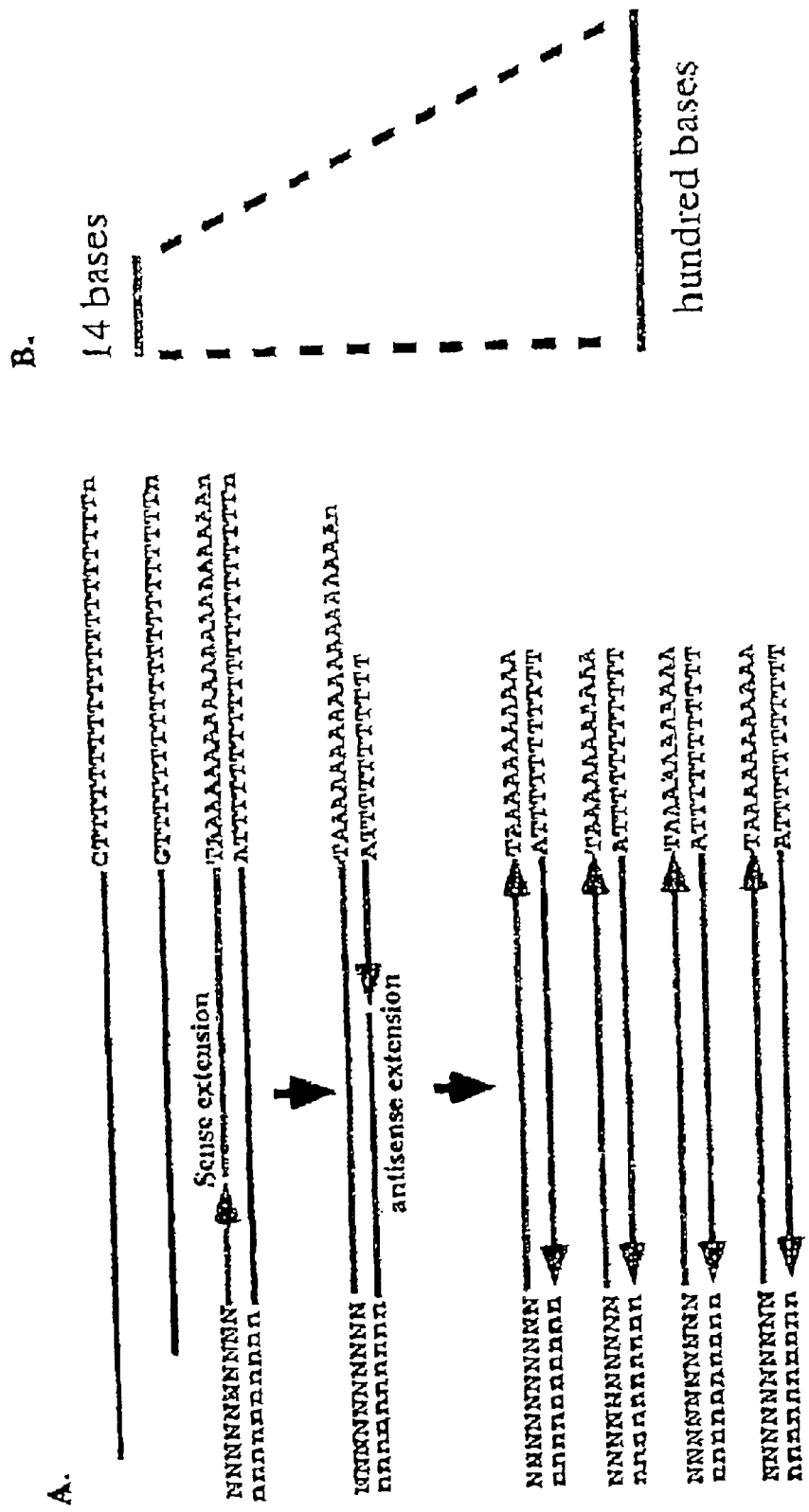
FIG. 1. Schematic for GLGI.

The inventors have developed a technique called the Generation of Longer cDNA fragments from SAGE tags for Gene Identification (GLGI), which converts SAGE tags, which are about 10 base pairs in length, into their corresponding 3' cDNA fragments covering hundred bases. The sense primer used comprises about 10 bases corresponding to a SAGE Tag and the antisense primer comprises a single base anchored to an oligo-dT primer. The single base may be dA, dG, or dC. PCR amplification using the primers described above generates a cDNA fragment extending from the SAGE Tag toward the 3' end of the corresponding sequence.

Application of the GLGI technique solves two critical issues in the application of the SAGE technique: (i) longer fragments corresponding to novel SAGE tags can be generated for further studies; and (ii) distinct fragments corresponding to a single SAGE tags can be identified and distinguished. Thus, the development of the GLGI method provides several potential applications. First, it provides a strategy for even wider application of the SAGE technique for quantitative analysis of global gene expression. Second, it can be used to identify the 3' cDNA sequence from any exon within a gene. These exons include ones predicted by bioinformatic tools. Third, a combined application of SAGE/GLGI can be used to complete the catalogue of the expressed genes in human and in other eukaryotic species. And fourth, a combined application of SAGE/GLGI can be applied to define the 3' boundary of expressed genes in the genomic sequences in human and in other eukaryotic genomes.

In the present invention the GLGI technique is further developed herein to identify genes encoding isolated proteins. Isolated proteins are digested by methods known to one of ordinary skill in the art. The protein fragments are then used to obtain nucleotide sequences encoding them. These relatively small nucleotide sequences are then used in GLGI wherein a DNA amplification reaction is performed using these nucleotide sequences as sense primers and using a single-base anchored poly-dT sequence as an anti-sense primer. This allows the amplification of DNA towards the 3' end of the gene encoding the isolated protein. Thus, the combination of GLGI with peptide/protein sequencing provides a novel method for gene identification starting with an isolated protein.

The GLGI method is still further developed herein into a high-throughput method for simultaneously converting a large set of SAGE tags into their 3' cDNAs thereby simultaneously characterizing a set of SAGE tag fragments. The method provides for generation of cDNA fragments using a 3' anchored oligo dT primer for first strand synthesis from a RNA sample, digesting this cDNA with an enzyme and isolating and amplifying 3' cDNA fragments. Re-amplifying the 3'cDNA fragments in a multi-well format by GLGI amplification generates longer cDNA fragments corresponding to multiple SAGE tags. Cloning and sequencing then allows identification of the gene. This procedure is simple, rapid, efficient and low-cost and therefore provides a tool for large-scale identification of expressed genes. Thus, genes of eukaryotic origin, such as human genes may be identified at an accelerated rate.

B. Serial Analysis of Gene Expression (SAGE)

The method for serial analysis of gene expression is described in U.S. Pat. No. 5,866,330 to Kinzler et al., which is incorporated herein by reference. The method involves the identification of a short nucleotide sequence tag at a defined position in a messenger RNA. The tag is used to identify the corresponding transcript and gene from which it was transcribed. By utilizing concatenated tags a rapid quantitative and qualitative analysis of expressed genes is possible. SAGE is thus useful as a gene discovery tool for the identification of known genes and novel sequence tags corresponding to novel transcripts and genes.

C. Oligonucleotide Probes and Primers

The present invention, in various aspects, will involve the use of nucleic acid hybridization. Hybridization occurs between nucleic acids that have a given degree of "complementarity." Nucleic acid sequences that are "complementary" are those that are capable of base-pairing according to the standard Watson-Crick complementary rules. As used herein, the term "complementary sequences" means nucleic acid sequences that are substantially identical, or as defined as being capable of annealing to a target nucleic acid segment being described under relatively stringent conditions such as those described herein.

The term primer, as defined herein, is meant to encompass any nucleic acid that is capable of priming the synthesis of a nascent nucleic acid in a template-dependent process. Typically, primers are oligonucleotides from ten to twenty-five base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

Primers should be of sufficient length to provide specific annealing to a RNA or DNA tissue sample. The use of a primer of between about 10, 11, 12, 13, 14, 15, 16, 17, 18, 19, 20, 20–25, 25–30, 30–35 and 35–40 nucleotides in length allows the formation of a duplex molecule that is both stable and selective. Of particular importance are SAGE derived primers which range from about 10 to 30 bases.

As a general rule, shorter oligomers are easier to make. However, numerous other factors are involved in determining usefulness. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 300, 500, 600, 700, 800, and longer are contemplated as well. Accordingly, nucleotide sequences may be selected for their ability to selectively form duplex molecules with complementary stretches of genes or RNAs or to provide primers for amplification of DNA or RNA from cells, cell lysates and tissues. The method of using probes and primers of the present invention is in the selective amplification and detection of genes, changes in gene expression, changes in mRNA expression wherein one could be detecting virtually any gene or genes of interest from any species. The target polynucleotide will be RNA molecules, mRNA, cDNA or amplified DNA. By varying the stringency of annealing, and the region of the primer, different degrees of homology may be discovered.

Primers may be chemically synthesized by methods well known within the art. Chemical synthesis methods allow for the placement of detectable labels such as fluorescent labels, radioactive labels, etc., to be placed virtually anywhere within the polynucleotide acid sequence. Solid phase method of synthesis also may be used.

The amplification primers may be attached to a solid-phase, for example, a latex bead, a magnetic bead, or the surface of a chip. Thus, the amplification carried out using these primers will be on a solid support/surface.

Furthermore, some primers of the present invention may have a recognition moiety attached. A wide variety of appropriate recognition means are known in the art, including fluorescent labels, radioactive labels, mass labels, affinity labels, chromophores, dyes, electroluminescence, chemiluminescence, enzymatic tags, or other ligands, such as avidin/biotin, or antibodies, which are capable of being detected and are described below.

1. Primer Design

According to the present invention, there are disclosed, in one aspect, oligo-dT primers for use in reverse transcription and amplification reactions. These primers are single-base 3'-anchored, i.e., contain a bases at their 3' ends. These bases are the singlets A, G or C. This creates a set of three primers.

The particular length of the primer is not believed to be critical, with the dT sequence ranging from about 10 to about 25 bases, with 11 being a preferred embodiment. In some embodiments, the primers are labeled with radioactive species ($^{32}P$, $^{14}C$, $^{35}S$, $^{3}H$, or other isotope), with a fluorophore (rhodamine, fluorescein, GFP) or a chemiluminescent label (luciferase).

Yet another primer specific to this invention is the sense prime that is comprised of a SAGE tag sequence. A discussion of these primers is provided U.S. Pat. No. 5,866,330 to Kinzler et al., which is incorporated herein by reference. Other exon-specific or gene-specific primers may be used for the sequencing and characterizing of amplified sequences.

2. Probes

In various contexts, it may be useful to use oligo- or polynucleotides as probes for complementary or hybridizing DNA or RNA molecules. In this regard, one may include particular "target" sequences in the oligos of the present invention in order to detect the products by probe hybridization. Alternatively, the probes may recognize unique sequences in the amplified regions upstream of the anchored oligo-dT primers.

3. Primer Synthesis

Oligonucleotide synthesis is performed according to standard methods. See, for example, Itakura and Riggs (1980). Additionally, U.S. Pat. No. 4,704,362; U.S. Pat. No. 5,221,619; U.S. Pat. No. 5,583,013 each describe various methods of preparing synthetic structural genes.

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference. Basically, chemical synthesis can be achieved by the diester method, the triester method, polynucleotides phosphorylase method and by solid-phase chemistry. These methods are discussed in further detail below.

Diester method. The diester method was the first to be developed to a usable state, primarily by Khorana and co-workers (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester method. The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purification's are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide phosphorylase method. This is an enzymatic method of DNA synthesis that can be used to synthesize many useful oligodeoxynucleotides (Gillam et al., 1978; Gillam et al., 1979). Under controlled conditions, polynucleotide phosphorylase adds predominantly a single nucleotide to a short oligodeoxynucleotide. Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-phase methods. Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic DNA synthesizers.

Phosphoramidite chemistry (Beaucage and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

D. Amplification

PCR™ In some embodiments, poly-A mRNA is isolated and reverse transcribed (referred to as RT) to obtain cDNA which is then used as a template for polymerase chain reaction (referred to as PCR™) based amplification. In other embodiments, cDNA may be obtained and used as a template for the PCR™ reaction. In PCR™, pairs of primers that selectively hybridize to nucleic acids are used under conditions that permit selective hybridization. The term primer, as used herein, encompasses any nucleic acid that is capable of priming the synthesis of a nascent nucleic acid in a template-dependent process. Primers may be provided in double-stranded or single-stranded form, although the single-stranded form is preferred.

The primers are used in any one of a number of template dependent processes to amplify the target-gene sequences present in a given template sample. One of the best known amplification methods is PCR™ which is described in detail in U.S. Pat. Nos. 4,683,195, 4,683,202 and 4,800,159, each incorporated herein by reference.

In PCR™, two primer sequences are prepared which are complementary to regions on opposite complementary strands of the target-gene(s) sequence. The primers will hybridize to form a nucleic-acid:primer complex if the target-gene(s) sequence is present in a sample. An excess of deoxynucleoside triphosphates are added to a reaction mixture along with a DNA polymerase, e.g., Taq polymerase, that facilitates template-dependent nucleic acid synthesis.

If the target-gene(s) sequence:primer complex has been formed, the polymerase will cause the primers to be extended along the target-gene(s) sequence by adding on nucleotides. By raising and lowering the temperature of the reaction mixture, the extended primers will dissociate from the target-gene(s) to form reaction products, excess primers will bind to the target-gene(s) and to the reaction products and the process is repeated. These multiple rounds of amplification, referred to as "cycles," are conducted until a sufficient amount of amplification product is produced.

Next, the amplification product is detected. In certain applications, the detection may be performed by visual means. Alternatively, the detection may involve indirect identification of the product via fluorescent labels, chemiluminescence, radioactive scintigraphy of incorporated radiolabel or incorporation of labeled nucleotides, mass labels or even via a system using electrical or thermal impulse signals (Affymax technology).

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641, filed Dec. 21, 1990.

E. Hybridization

Hybridization is the technique used to identify nucleic acid products by the nature of the complementarity of a target gene to the hybridization probe or primer. Varying degrees of probe/primer selectivity towards target sequence can be measured.

For applications requiring high selectivity, one typically will employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for detecting specific genes or specific mRNA transcripts. It is generally appreciated that conditions can be rendered more stringent by the addition of increasing amounts of formamide.

For certain applications, it is appreciated that lower stringency conditions are required. Under these conditions, hybridization may occur even though the sequences of probe/primer and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 $\mu$M $MgCl_2$, at temperatures ranging from approximately 40° C. to about 72° C.

The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe/primer molecules, hybridization is detected, or even quantified, by means of the label.

In general, it is envisioned that hybridization with respect to the primers described herein or in the context of probes will be useful both in solution hybridization, as in PCR™, for the priming of amplification reactions and for the detection of target or reference gene expression, as well as in embodiments employing a solid phase. In embodiments involving a solid phase, the test DNA (or RNA) can be adsorbed or otherwise affixed (for example, by affinity separation methods) to a selected matrix or surface. This fixed, single-stranded nucleic acid can then be subject to hybridization with selected probes or primers under desired conditions. Alternatively, the probe or primer may be fixed to the selected matrix or surface for gene detection. Suitable surfaces include chips, latex beads or plates.

F. cDNA Synthesis

In a preferred embodiment of the invention, the assay is employed for analyzing gene expression patterns using RNA as the starting template. The RNA template may be presented as either total cellular RNA or isolated mRNA. Both types of sample yield comparable results. In still further embodiments, other types of nucleic acids may serve as template in the assay, including genomic or extragenomic DNA, viral RNA or DNA, or nucleic acid polymers generated by non-replicative or artificial means.

In a preferred embodiment of the invention, RNA is converted to cDNA using a oligo-dT primer. Methods of reverse transcribing RNA into cDNA are well known, and described in Sambrook et al., 1989. Alternative methods for reverse transcription utilize thermostable DNA polymerases. These methods are described in WO90/07641. In alternative embodiments, avian myeloblastosis virus reverse transcriptase (AMV-RT), or Maloney murine leukemia virus reverse transcriptase (MoMLV-RT) may be used. Other enzymes are contemplated as well.

In another embodiment, RNA targets may be reverse transcribed using other non-specific primers, such as an anchored oligo-dT primer, or random sequence primers. An advantage of this embodiment is that the "unfractionated" quality of the mRNA sample is maintained because the sites of priming are non-specific, i.e., the products of this RT reaction will serve as template for any desired target in the subsequent PCR™ amplification. This allows samples to be archived in the form of DNA, which is more stable than RNA.

G. Sequencing

Methods for sequencing are well known in the art, in particular, the chain-termination technique pioneered by Sanger et al. in the mid-1970's. Recent developments have increased dramatically the number of bases that can be sequenced in a short period of time. The following U.S. patents, dealing with DNA sequencing, are incorporated by reference: U.S. Pat. Nos. 6,004,446; 5,985,556; 5,968,743; 5,876,934; 5,866,328; 5,858,671; 5,846,727; 5,821,060; 5,821,058; 5,817,797; 5,780,232; 5,755,943; 5,674,716; 5,639,608; 5,608,063; 5,523,206; 5,455,008; 5,432,065; 5,405,746; 5,360,523; 5,308,751; and 5,207,880.

H. Restriction Enzymes

Restriction-enzymes recognize specific short DNA sequences four to eight nucleotides long (see Table 1), and cleave the DNA at a site within this sequence. Restriction enzymes are used to cleave cDNA molecules at sites corresponding to various restriction-enzyme recognition sites. In context of this invention, the enzyme NlaIII is often used in the SAGE technique and the SAGE tags often are comprised of NlaIII recognition sequences. The sense primers in the present invention may further comprise a restriction enzyme recognition sequence, such as the BamHI sequence, to allow easier cloning amplified DNA fragments for further analysis.

As the sequence of the recognition site is known (see list below), primers can be designed comprising nucleotides corresponding to the recognition sequences. If the primer sets have in addition to the restriction recognition sequence, degenerate sequences corresponding to different combinations of nucleotide sequences, one can use the amplified cDNA fragments that have the particular restriction enzyme sequence for cloning the cDNA into cloning vectors. The list below exemplifies the currently known restriction enzymes that may be used in the invention.

TABLE 1

| Restriction Enzymes | | |
|---|---|---|
| Enzyme Name | Recognition Sequence | |
| AatII | GACGTC | |
| Acc65 I | GGTACC | |
| Acc I | GTMKAC | |
| Aci I | CCGC | |
| Acl I | AACGTT | |
| Afe I | AGCGCT | |
| Afl II | CTTAAG | |
| Afl III | ACRYGT | |
| Age I | ACCGGT | |
| Ahd I | GACNNNNNGTC | (SEQ ID NO:36) |
| Alu I | AGCT | |
| Alw I | GGATC | |
| AlwN I | CAGNNNCTG | |

TABLE 1-continued

| Restriction Enzymes | | |
|---|---|---|
| Enzyme Name | Recognition Sequence | |
| Apa I | GGGCCC | |
| ApaL I | GTGCAC | |
| Apo I | RAATTY | |
| Asc I | GGCGCGCC | |
| Ase I | ATTAAT | |
| Ava I | CYCGRG | |
| Ava II | GGWCC | |
| Avr II | CCTAGG | |
| Bae I | NACNNNNGTAPyCN | (SEQ ID NO:37) |
| BamH I | GGATCC | |
| Ban I | GGYRCC | |
| Ban II | GRGCYC | |
| Bbs I | GAAGAC | |
| Bbv I | GCAGC | |
| BbvC I | CCTCAGC | |
| Bcg I | CGANNNNNNTGC | (SEQ ID NO:38) |
| BciV I | GTATCC | |
| Bcl I | TGATCA | |
| Bfa I | CTAG | |
| Bgl I | GCCNNNNNGGC | (SEQ ID NO:39) |
| Bgl II | AGATCT | |
| Blp I | GCTNAGC | |
| Bmr I | ACTGGG | |
| Bpm I | CTGGAG | |
| BsaA I | YACGTR | |
| BsaB I | GATNNNNATC | (SEQ ID NO:40) |
| BsaH I | GRCGYC | |
| Bsa I | GGTCTC | |
| BsaJ I | CCNNGG | |
| BsaW I | WCCGGW | |
| BseR I | GAGGAG | |
| Bsg I | GTGCAG | |
| BsiE I | CGRYCG | |
| BsiHKA I | GWGCWC | |
| BsiW I | CGTACG | |
| Bsl I | CCNNNNNNNGG | (SEQ ID NO:41) |
| BsmA I | GTCTC | |
| BsmB I | CGTCTC | |

TABLE 1-continued

| Restriction Enzymes | |
|---|---|
| Enzyme Name | Recognition Sequence |
| BsmF I | GGGAC |
| Bsm I | GAATGC |
| BsoB I | CYCGRG |
| Bsp1286 I | GDGCHC |
| BspD I | ATCGAT |
| BspE I | TCCGGA |
| BspH I | TCATGA |
| BspM I | ACCTGC |
| BsrB I | CCGCTC |
| BsrD I | GCAATG |
| BsrF I | RCCGGY |
| BsrG I | TGTACA |
| Bsr I | ACTGG |
| BssH II | GCGCGC |
| BssK I | CCNGG |
| Bst4C I | ACNGT |
| BssS I | CACGAG |
| BstAP I | GCANNNNNTGC (SEQ ID NO:42) |
| BstB I | TTCGAA |
| BstE II | GGTNACC |
| BstF5 I | GGATGNN |
| BstN I | CCWGG |
| BstU I | CGCG |
| BstX I | CCANNNNNNTGG (SEQ ID NO:43) |
| BstY I | RGATCY |
| BstZ17 I | GTATAC |
| Bsu36 I | CCTNAGG |
| Btg I | CCPuPyGG |
| Btr I | CACGTG |
| Cac8 I | GCNNGC |
| Cla I | ATCGAT |
| Dde I | CTNAG |
| Dpn I | GATC |
| Dpn II | GATC |
| Dra I | TTTAAA |
| Dra III | CACNNNGTG |
| Drd I | GACNNNNNNGTC (SEQ ID NO:44) |

TABLE 1-continued

| Restriction Enzymes | |
|---|---|
| Enzyme Name | Recognition Sequence |
| Eae I | YGGCCR |
| Eag I | CGGCCG |
| Ear I | CTCTTC |
| Eci I | GGCGGA |
| EcoN I | CCTNNNNNAGG (SEQ ID NO:45) |
| EcoO109 I | RGGNCCY |
| EcoR I | GAATTC |
| EcoR V | GATATC |
| Fau I | CCCGCNNNN |
| Fnu4H I | GCNGC |
| Fok I | GGATG |
| Fse I | GGCCGGCC |
| Fsp I | TGCGCA |
| Hae II | RGCGCY |
| Hae III | GGCC |
| Hga I | GACGC |
| Hha I | GCGC |
| Hinc II | GTYRAC |
| Hind III | AAGCTT |
| Hinf I | GANTC |
| HinP1 I | GCGC |
| Hpa I | GTTAAC |
| Hpa II | CCGG |
| Hph I | GGTGA |
| Kas I | GGCGCC |
| Kpn I | GGTACC |
| Mbo I | GATC |
| Mbo II | GAAGA |
| Mfe I | CAATTG |
| Mlu I | ACGCGT |
| Mly I | GAGTCNNNNN (SEQ ID NO:46) |
| Mnl I | CCTC |
| Msc I | TGGCCA |
| Mse I | TTAA |
| Msl I | CAYNNNNRTG (SEQ ID NO:47) |
| MspA1 I | CMGCKG |
| Msp I | CCGG |
| Mwo I | GCNNNNNNNGC (SEQ ID NO:48) |

TABLE 1-continued

Restriction Enzymes

| Enzyme Name | Recognition Sequence | |
|---|---|---|
| Nae I | GCCGGC | |
| Nar I | GGCGCC | |
| Nci I | CCSGG | |
| Nco I | CCATGG | |
| Nde I | CATATG | |
| NgoMI V | GCCGGC | |
| Nhe I | GCTAGC | |
| Nla III | CATG | |
| Nla IV | GGNNCC | |
| Not I | GCGGCCGC | |
| Nru I | TCGCGA | |
| Nsi I | ATGCAT | |
| Nsp I | RCATGY | |
| Pac I | TTAATTAA | |
| PaeR7 I | CTCGAG | |
| Pci I | ACATGT | |
| PflF I | GACNNNGTC | |
| PflM I | CCANNNNNTGG | (SEQ ID NO:49) |
| PleI | GAGTC | |
| Pme I | GTTTAAAC | |
| Pml I | CACGTG | |
| PpuM I | RGGWCCY | |
| PshA I | GACNNNNGTC | (SEQ ID NO:50) |
| Psi I | TTATAA | |
| PspG I | CCWGG | |
| PspOM I | GGGCCC | |
| Pst I | CTGCAG | |
| Pvu I | CGATCG | |
| Pvu II | CAGCTG | |
| Rsa I | GTAC | |
| Rsr II | CGGWCCG | |
| Sac I | GAGCTC | |
| Sac II | CCGCGG | |
| Sal I | GTCGAC | |
| Sap I | GCTCTTC | |
| Sau3A I | GATC | |
| Sau96 I | GGNCC | |

TABLE 1-continued

Restriction Enzymes

| Enzyme Name | Recognition Sequence | |
|---|---|---|
| Sbf I | CCTGCAGG | |
| Sca I | AGTACT | |
| ScrF I | CCNGG | |
| SexA I | ACCWGGT | |
| SfaN I | GCATC | |
| Sfc I | CTRYAG | |
| Sfi I | GGCCNNNNNGGCC | (SEQ ID NO:51) |
| Sfo I | GGCGCC | |
| SgrA I | CRCCGGYG | |
| Sma I | CCCGGG | |
| Sml I | CTYRAG | |
| SnaB I | TACGTA | |
| Spe I | ACTAGT | |
| Sph I | GCATGC | |
| Ssp I | AATATT | |
| Stu I | AGGCCT | |
| Sty I | CCWWGG | |
| Swa I | ATTTAAAT | |
| Taq I | TCGA | |
| Tfi I | GAWTC | |
| Tli I | CTCGAG | |
| Tse I | GCWGC | |
| Tsp45 I | GTSAC | |
| Tsp509 I | AATT | |
| TspR I | CAGTG | |
| Tth111 I | GACNNNGTC | |
| Xba I | TCTAGA | |
| Xcm I | CCANNNNNNNNNTGG | (SEQ ID NO:52) |
| Xho I | CTCGAG | |
| Xma I | CCCGGG | |
| Xmn I | GAANNNNTTC | (SEQ ID NO:53) |

I. Polymerases

1. Reverse Transcriptases

According to the present invention, a variety of different reverse transcriptases may be utilized. The following are representative examples.

M-MLV Reverse Transcriptase. M-MLV (Moloney Murine Leukemia Virus Reverse Transcriptase) is an RNA-dependent DNA polymerase requiring a DNA primer and an RNA template to synthesize a complementary DNA strand. The enzyme is a product of the pol gene of M-MLV and consists of a single subunit with a molecular weight of 71 kDa. M-MLV RT has a weaker intrinsic RNase H activity than Avian Myeloblastosis Virus (AMV) reverse transcriptase which is important for achieving long full-length complementary DNA (>7 kB).

M-MLV can be use for first strand cDNA synthesis and primer extensions. Storage recommend at −20° C. in 20 mM Tris-HCl (pH 7.5), 0.2M NaCl, 0.1 mM EDTA, 1 mM DTT, 0.01% Nonidet® P-40, 50% glycerol. The standard reaction conditions are 50 mM Tris-HCl (pH 8.3), 7 mM $MgCl_2$, 40 mM KCl, 10 mM DTT, 0.1 mg/ml BSA, 0.5 mM $^3$H-dTTP, 0.025 mM oligo(dT)$_{50}$, 0.25 mM poly(A)$_{400}$ at 37° C.

M-MLV Reverse Transcriptase, RNase H Minus. This is a form of Moloney murine leukemia virus reverse transcriptase (RNA-dependent DNA polymerase) which has been genetically altered to remove the associated ribonuclease H activity (Tanese and Goff, 1988). It can be used for first strand cDNA synthesis and primer extension. Storage is at 20° C. in 20 mM Tris-HCl (pH 7.5), 0.2M NaCl, 0.1 mM EDTA, 1 mM DTT, 0.01% Nonidet® P-40, 50% glycerol.

AMV Reverse Transcriptase. Avian Myeloblastosis Virus reverse transcriptase is a RNA dependent DNA polymerase that uses single-stranded RNA or DNA as a template to synthesize the complementary DNA strand (Houts et al., 1979). It has activity at high temperature (42° C.–50° C.). This polymerase has been used to synthesize long cDNA molecules.

Reaction conditions are 50 mM Tris-HCl (pH 8.3), 20 mM KCl, 10 mM $MgCl_2$, 500 μM of each dNTP, 5 mM dithiothreitol, 200 μg/ml oligo-dT$_{(12-18)}$, 250 μg/ml polyadenylated RNA, 6.0 pMol $^{32}$P-dCTP, and 30 U enzyme in a 7 μl volume. Incubate 45 min at 42° C. Storage buffer is 200 mM $KPO_4$ (pH 7.4), 2 mM dithiothreitol, 0.2% Triton X-100, and 50% glycerol. AMV may be used for first strand cDNA synthesis, RNA or DNA dideoxy chain termination sequencing, and fill-ins or other DNA polymerization reactions for which Klenow polymerase is not satisfactory (Maniatis et al., 1976).

2. DNA Polymerases

The present invention also contemplates the use of various DNA polymerase. Exemplary polymerases are described below.

Bst DNA Polymerase, Large Fragment. Bst DNA Polymerase Large Fragment is the portion of the *Bacillus stearothermophilus* DNA Polymerase protein that contains the 5'→3' polymerase activity, but lacks the 5'→3' exonuclease domain. BST Polymerase Large Fragment is prepared from an *E. coli* strain containing a genetic fusion of the *Bacillus stearothermophilus* DNA Polymerase gene, lacking the 5'→3' exonuclease domain, and the gene coding for *E. coli* maltose binding protein (MBP). The fusion protein is purified to near homogeneity and the MBP portion is cleaved off in vitro. The remaining polymerase is purified free of MBP (Iiyy et al., 1991).

Bst DNA polymerase can be used in DNA sequencing through high GC regions (Hugh & Griffin, 1994; McClary et al., 1991) and Rapid Sequencing from nanogram amounts of DNA template (Mead et al., 1991). The reaction buffer is 1× ThermoPol Butter (20 mM Tris-HCl (pH 8.8 at 25° C.), 10 mM KCl, 10 mM $(NH_4)_2SO_4$, 2 mM $MgSO_4$, 0.1% Triton X-100). Supplied with enzyme as a 10× concentrated stock.

Bst DNA Polymerase does not exhibit 3'→5' exonuclease activity. 100 μ/ml BSA or 0.1% Triton X-100 is required for long term storage. Reaction temperatures above 70° C. are not recommended. Heat inactivated by incubation at 80° C. for 10 min. Bst DNA Polymerase cannot be used for thermal cycle sequencing. Unit assay conditions are 50 mM KCl, 20 mM Tris-HCl (pH 8.8), 10 mM $MgCl_2$, 30 nM M13 mp18 ssDNA, 70 nM M13 sequencing primer (−47) 24 mer (NEB #1224), 200 μM daTP, 200 μM dCTP, 200 μM dGTP, 100 μM $^3$H-dTTP, 100 μg/ml BSA and enzyme. Incubate at 65° C. Storage buffer is 50 mM KCl, 10 mM Tris-HCl (pH 7.5), 1 mM dithiothreitol, 0.1 mM EDTA, 0.1% Triton-X-100 and 50% glycerol. Storage is at −20° C.

VENT$_R$® DNA Polymerase and VENT$_R$® (exo$^-$) DNA Polymerase. Vent$_R$ DNA Polymerase is a high-fidelity thermophilic DNA polymerase. The fidelity of Vent$_R$ DNA Polymerase is 5–15-fold higher than that observed for Taq DNA Polymerase (Mattila et al., 1991; Eckert and Kunkel, 1991). This high fidelity derives in part from an integral 3'→5' proofreading exonuclease activity in Vent$_R$ DNA Polymerase (Mattila et al., 1991; Kong et al., 1993). Greater than 90% of the polymerase activity remains following a 1 h incubation at 95° C.

Vent$_R$ (exo−) DNA Polymerase has been genetically engineered to eliminate the 3'→5' proofreading exonuclease activity associated with Vent$_R$ DNA Polymerase (Kong et al., 1993). This is the preferred form for high-temperature dideoxy sequencing reactions and for high yield primer extension reactions. The fidelity of polymerization by this form is reduced to a level about 2-fold higher than that of Taq DNA Polymerase (Mattila et al., 1991; Eckert & Kunkel, 1991). Vent$_R$ (exo−) DNA Polymerase is an excellent choice for DNA sequencing and is included in Circum-Vent Sequencing Kit (see pages 118 and 121).

Both Vent$_R$ and Vent$_R$ (exo−) are purified from strains of *E. coli* that carry the Vent DNA Polymerase gene from the archaea *Thermococcus litoralis* (Perler et al., 1992). The native organism is capable of growth at up to 98° C. and was isolated from a submarine thermal vent (Belkin and Jannasch, 1985). They are useful in primer extension, thermal cycle sequencing and high temperature dideoxy-sequencing.

DEEP VENT$_R$™ DNA Polymerase and DEEP VENT$_R$™ (exo$^-$) DNA Polymerase. Deep Vent$_R$ DNA Polymerase is the second high-fidelity thermophilic DNA polymerase available from New England Biolabs. The fidelity of Deep Vent$_R$ DNA Polymerase is derived in part from an integral 3'→5' proofreading exonuclease activity. Deep Vent$_R$ is even more stable than Vent$_R$ at temperatures of 95 to 100° C. (see graph).

Deep Vent$_R$ (exo−) DNA Polymerase has been genetically engineered to eliminate the 3'→5' proofreading exonuclease activity associated with Deep Vent$_R$ DNA Polymerase. This exo− version can be used for DNA sequencing but requires different dNTP/ddNTP ratios than those used with Vent$_R$ (exo−) DNA Polymerase. Both Deep Vent$_R$ and Deep Vent$_R$ (exo−) are purified from a strain of *E. coli* that carries the Deep Vent$_R$ DNA Polymerase gene from *Pyrococcus* species GB-D (Perler et al., 1996). The native organism was isolated from a submarine thermal vent at 2010 meters (Jannasch et al., 1992) and is able to grow at temperatures as high as 104° C. Both enzymes can be used in primer extension, thermal cycle sequencing and high temperature dideoxy-sequencing.

T7 DNA Polymerase (unmodified). T7 DNA polymerase catalyzes the replication of T7 phage DNA during infection. The protein dimer has two catalytic activities: DNA polymerase activity and strong 3'→5' exonuclease (Hori et al., 1979; Engler et al., 1983; Nordstrom et al., 1981). The high fidelity and rapid extension rate of the enzyme make it particularly useful in copying long stretches of DNA template.

T7 DNA Polymerase consists of two subunits: T7 gene 5 protein (84 kilodaltons) and *E. coli* thioredoxin (12 kilodaltons) (Hori et al., 1979; Studier et al., 1990; Grippo & Richardson, 1971; Modrich & Richardson, 1975; Adler & Modrich, 1979). Each protein is cloned and overexpressed in a T7 expression system in *E. coli* (Studier et al., 1990). It can be used in second strand synthesis in site-directed mutagenesis protocols (Bebenek & Kunkel, 1989).

The reaction buffer is 1× T7 DNA Polymerase Buffer (20 mM Tris-HCl (pH 7.5), 10 mM $MgCl_2$, 1 mM dithiothreitol). Supplement with 0.05 mg/ml BSA and dNTPs. Incubate at 37° C. The high polymerization rate of the enzyme makes long incubations unnecessary. T7 DNA Polymerase is not suitable for DNA sequencing.

Unit assay conditions are 20 mM Tris-HCl (pH 7.5), 10 mM $MgCl_2$, 1 mM dithiothreitol, 0.05 mg/ml BSA, 0.15 mM each dNTP, 0.5 mM heat denatured calf thymus DNA and enzyme. Storage conditions are 50 mM $KPO_4$ (pH 7.0), 0.1 mM EDTA, 1 mM dithiothreitol and 50% glycerol. Store at −20° C.

DNA Polymerase I (*E. coli*). DNA Polymerase I is a DNA-dependent DNA polymerase with inherent 3'→5' and 5'→3' exonuclease activities (Lehman, 1981). The 5'→3' exonuclease activity removes nucleotides ahead of the growing DNA chain, allowing nick-translation. It is isolated from *E. Coli* CM 5199, a lysogen carrying λpolA transducing phage (obtained from N. E. Murray) (Murray & Kelley, 1979). The phage in this strain was derived from the original polA phage encoding wild-type Polymerase I.

Applications include nick translation of DNA to obtain probes with a high specific activity (Meinkoth and Wahl, 1987) and second strand synthesis of cDNA (Gubler & Hoffmann, 1983; D'Alessio & Gerard, 1988). The reaction buffer is *E. coli* Polymerase I/Klenow Buffer (10 mM Tris-HCl (pH 7.5), 5 mM $MgCl_2$, 7.5 mM dithiothreitol). Supplement with dNTPs.

DNase I is not included with this enzyme and must be added for nick translation reactions. Heat inactivation is for 20 min at 75° C. Unit assay conditions are 40 mM $KPO_4$ (pH 7.5), 6.6 mM $MgCl_2$, 1 mM 2-mercaptoethanol, 20 $\mu$M dAT copolymer, 33 $\mu$M dATP and 33 $\mu$M $^3$H-dTTP. Storage conditions are 0.1 M $KPO_4$ (pH 6.5), 1 mM dithiothreitol, and 50% glycerol. Store at −20° C.

DNA Polymerase I, Large (Klenow) Fragment. Klenow fragment is a proteolytic product of *E. Coli* DNA Polymerase I that retains polymerization and 3'→5' exonuclease activity, but has lost 5'→3' exonuclease activity. Klenow retains the polymerization fidelity of the holoenzyme without degrading 5' termini.

A genetic fusion of the *E. coli* polA gene, that has its 5'→3' exonuclease domain genetically replaced by maltose binding protein (MBP). Klenow Fragment is cleaved from the fusion and purified away from MBP. The resulting Klenow fragment has the identical amino and carboxy termini as the conventionally prepared Klenow fragment.

Applications include DNA sequencing by the Sanger dideoxy method (Sanger et al., 1977), fill-in of 3' recessed ends (Sambrook et al., 1989), second-strand cDNA synthesis, random priming labeling and second strand synthesis in mutagenesis protocols (Gubler, 1987).

Reactions conditions are 1× *E. coli* Polymerase I/Klenow Buffer (10 mM Tris-HCl (pH 7.5), 5 mM MgCl2, 7.5 mM dithiothreitol). Supplement with dNTPs (not included). Klenow fragment is also 50% active in all four standard NEBuffers when supplemented with dNTPs. Heat inactivated by incubating at 75° C. for 20 min. Fill-in conditions: DNA should be dissolved, at a concentration of 50 $\mu$g/ml, in one of the four standard NEBuffers (1×) supplemented with 33 $\mu$M each dNTP. Add 1 unit Klenow per $\mu$g DNA and incubate 15 min at 25° C. Stop reaction by adding EDTA to 10 mM final concentration and heating at 75° C. for 10 min. Unit assay conditions 40 mM KPO4 (pH 7.5), 6.6 mM MgCl2, 1 mM 2-mercaptoethanol, 20 $\mu$M dAT copolymer, 33 $\mu$M dATP and 33 $\mu$M $^3$H-dTTP. Storage conditions are 0.1 M $KPO_4$ (pH 6.5), 1 mM dithiothreitol, and 50% glycerol. Store at −20° C.

Klenow Fragment (3'→5' exo$^-$). Klenow Fragment (3'→5' exo−) is a proteolytic product of DNA Polymerase I which retains polymerase activity, but has a mutation which abolishes the 3'→5' exonuclease activity and has lost the 5'→3' exonuclease (Derbyshire et al., 1988).

A genetic fusion of the *E. coli* polA gene, that has its 3'→5' exonuclease domain genetically altered and 5'→3' exonuclease domain replaced by maltose binding protein (MBP). Klenow Fragment exo− is cleaved from the fusion and purified away from MBP. Applications include random priming labeling, DNA sequence by Sanger dideoxy method (Sanger et al., 1977), second strand cDNA synthesis and second strand synthesis in mutagenesis protocols (Gubler, 1987).

Reaction buffer is 1× *E. coli* Polymerase I/Klenow Buffer (10 mM Tris-HCl (pH 7.5), 5 mM $MgCl_2$, 7.5 mM dithiothreitol). Supplement with dNTPs. Klenow Fragment exo− is also 50% active in all four standard NEBuffers when supplemented with dNTPs. Heat inactivated by incubating at 75° C. for 20 min. When using Klenow Fragment (3'→5' exo−) for sequencing DNA using the dideoxy method of Sanger et al. (1977), an enzyme concentration of 1 unit/5 $\mu$l is recommended.

Unit assay conditions are 40 mM $KPO_4$ (pH 7.5), 6.6 mM $MgCl_2$, 1 mM 2-mercaptoethanol, 20 $\mu$M dAT copolymer, 33 $\mu$M dATP and 33 $\mu$M $^3$H-dTTP. Storage conditions are 0.1 M $KPO_4$ (pH 7.5), 1 mM dithiothreitol, and 50% glycerol. Store at −20° C.

T4 DNA Polymerase. T4 DNA Polymerase catalyzes the synthesis of DNA in the 5'→3' direction and requires the presence of template and primer. This enzyme has a 3'→5' exonuclease activity which is much more active than that found in DNA Polymerase I. Unlike *E. Coli* DNA Polymerase I, T4 DNA Polymerase does not have a 5'→3' exonuclease function.

Purified from a strain of *E. coli* that carries a T4 DNA Polymerase overproducing plasmid. Applications include removing 3' overhangs to form blunt ends (Tabor & Struhl, 1989; Sambrook et al., 1989), 5' overhang fill-in to form blunt ends (Tabor & Struhl, 1989; Sambrook et al., 1989), single strand deletion subcloning (Dale et al., 1985), second strand synthesis in site-directed mutagenesis (Kunkel et al., 1987), and probe labeling using replacement synthesis (Tabor & Struhl, 1989; Sambrook et al., 1989).

The reaction buffer is 1× T4 DNA Polymerase Buffer (50 mM NaCl, 10 mM Tris-HCl, 10 mM $MgCl_2$, 1 mM dithiothreitol (pH 7.9 at 25° C.)). Supplement with 40 $\mu$g/ml BSA and dNTPs (not included in supplied 10× buffer). Incubate at temperature suggested for specific protocol.

It is recommended to use 100 $\mu$M of each dNTP, 1–3 units polymerase/$\mu$g DNA and incubation at 12° C. for 20 min in the above reaction buffer (Tabor & Struhl, 1989; Sambrook et al., 1989). Heat inactivated by incubating at 75° C. for 10 min. T4 DNA Polymerase is active in all four standard NEBuffers when supplemented with dNTPs.

Unit assay conditions are 50 mM NaCl, 10 mM Tris-HCl, 10 mM $MgCl_2$, 1 mM dithiothreitol (pH 7.9 at 25° C.), 33 $\mu$M dATP, dCTP and dGTP, 33 $\mu$M $^3$H dTTP, 70 $\mu$g/ml denatured calf thymus DNA, and 170 $\mu$g/ml BSA. Note: These are not suggested reaction conditions; refer to Reaction Buffer. Storage conditions are 100 mM $KPO_4$ (pH 6.5), 10 mM 2-mercaptoethanol and 50% glycerol. Store at −20° C.

3. RNA Polymerases

RNA polymerases for use in the present invention are exemplified as follows.

T7 RNA Polymerase SP6 RNA Polymerase and T3 RNA Polymerase. Initiation of transcription with T7, SP6 RNA and T3 RNA Polymerase Polymerases is highly specific for the T7 and SP6 phage promoters, respectively. Cloning vectors have been developed which direct transcription from the T7 SP6 or T3 promoter through polylinker cloning sites (Schenborn & Meirendorf, 1985). These vectors allow in vitro synthesis of defined RNA transcripts from a cloned DNA sequence. Under optimal conditions, greater than 700 moles of T7 RNA transcript can be synthesized per mole of DNA template (Noren et al., 1990). RNA produced using the SP6 and T7 RNA polymerases is biologically active as mRNA (Krieg & Melton, 1984) and can be accurately spliced (Green et al., 1983). Anti-sense RNA, produced by reversing the orientation of the cloned DNA insert, has been shown to specifically block mRNA translation in vivo (Melton, 1985).

Labeled single-stranded RNA transcripts of high specific activity are simple to prepare with T7 and SP6 RNA polymerases (Sambrook et al., 1989). Increased levels of detection in nucleic acid hybridization reactions can also be obtained due to the greater stability of RNA:DNA hybrids with respect to RNA:RNA or DNA:DNA hybrids (Zinn et al., 1983).

SP6 RNA Polymerase is isolated form SP6 phage-infected *Salmonella typhimurium* LT2Z (Butler & Chamberlin, 1982). T7 RNA Polymerase is isolated from *E. coli* BL21 carrying the plasmid pAR1219 which contains T7 gene 1 under the control of the inducible lac UV6 promoter (Davanloo et al., 1984). Applications include preparation of radiolabeled RNA probes (Sambrook et al., 1989), RNA generation for in vitro translation (Sambrook et al., 1989), RNA generation for studies of RNA structure, processing and catalysis (Sambrook et al., 1989) and expression control via antisense RNA.

Reaction 1× RNA Polymerase Buffer: (40 mM Tris-HCl (pH 7.9), 6 mM $MgCl_2$, 2 mM spermidine, 10 mM dithiothreitol). Supplement with 0.5 mM each ATP, UTP, GTP, CTP (not included) and DNA template containing the appropriate promoter. Incubate at 37° C. (T7 RNA polymerase) or 40° C. (SP6 RNA polymerase).

Dithiothreitol is required for activity. Both enzymes are extremely sensitive to salt inhibition. For best results overall salt concentration should not exceed 50 mM. SP6 RNA polymerase is 30% more active at 40° C. than at 37° C. Higher yields of RNA may be obtained by raising NTP concentrations (up to 4 mM each). $Mg^{2+}$ concentration should be raised to 4 mM above the total NTP concentration. Additionally, inorganic pyrophosphatase should be added to a final concentration of 4 units/ml. SP6 RNA polymerase is supplied with a control template (NEB#207B). The template is a pSP64 vector containing a 1.38 kB insert, linearized at 3 different restriction sites. Transcription with SP6 RNA polymerase results in three runoff fragments of 1.38 kB, 0.55 kB and 0.22 kB.

Storage conditions are 100 mM NaCl, 50 mM Tris-HCl (pH 7.9), 1 mM EDTA, 20 mM 2-mercaptoethanol, 0.1% Triton-X-100 and 50% glycerol. Store at −20° C.

T3 RNA polymerase is a DNA dependent RNA polymerase which exhibits extremely high specificity for T3 promoter sequences. The enzyme will incorporates 32P, 35S and 3H-labeled nucleotide triphosphates. It is used in the synthesis of RNA transcripts for hybridization probes in vitro translation, RNase protection assays or RNA processing substrates.

One unit of T3 RNA polymerase is defined as the amount of enzyme required to catalyze the incorporation of 5 nmol of CTP into acid insoluble product in 60 minutes at 37° C. in a total volume of 100 μl. The reaction conditions are as follows, 40 mM Tris-HCl (pH 7.9), 6 mM $MgCl_2$, 10 mM DTT, 10 mM NaCl, 2 mM spermidine, 0.5% Tween®-20, 0.5 mM each ATP, GTP, DTP, and UTP, 0.5 μCi [$^3$H] CTP, and 2 μg supercoiled pSP6/T3 Vector DNA. Promega provide a T3 RNA polymerase extracted from recombinant *E. coli*.

J. Analysis of Sequence Data/Bioinformatics

The sequences generated using GLGI can be used to match gene databases (e.g., GenBank, EMBL, DDBJ, UniGene Human Database). Each sequence will be identified as a known gene, EST sequence, or novel sequences without matches. There are many bioinformatic tools used for gene prediction in genomic DNA, for example, GenScan™ program.

K. Protein Purification

In context of the present invention it will be desirable to isolate and purify proteins. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) and FPLC are characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

L. Sequencing Proteins

Protein sequencing may be carried out by techniques well known in the art such as those involving the sequential removal of amino acids from one end of the protein and identifying each removed amino acid in turn (Edman's Degradation). Other techniques to obtain amino acid sequence information use mass spectrometry, typically using fast atom bombardment to ionize the sample. In fast atom bombardment, a sample dissolved in a liquid is bombarded with atoms or ions. Charged molecules resulting from this process are directed into the spectrometer and detected. An example of this technique is described in the text entitled "Macro Molecular Sequencing and Synthesis Selected Methods and Applications", 1988, published by Alan R. Liss, Inc., specifically at pages 83 to 99 in an article in such text entitled "Mass Spectrometry in Bio-Pharmaceutical Research" by Steven A. Carr et al. 1988, Several modifications of these techniques are well known to the skilled artisan and any of the techniques used for protein sequencing may be used in context of the present invention.

Typically protein sequencing methods involve digesting the large protein molecule into smaller fragments. These fragments are then separated or purified and then subject to the sequencing method.

1. Digesting Proteins

Digesting purified and/or isolated protein molecules to obtain smaller fragments can be carried out using proteolytic enzymes, known as proteases, to obtain a variety of N-terminal, C-terminal and internal fragments. Some of the well known proteases include trypsin, chymotyrpsin, elastase, collagenase, leupeptin, and endoproteinases. Other protein digesting enzymes are also present and may be used in this invention and are well known to one of ordinary skill in the art and. Examples of fragments may include contiguous residues of the protein sequence 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, or more amino acids in length.

2. Separating Protein Fragments

These digested protein fragments may be separated or further purified according to known methods, such as precipitation e.g. ammonium sulfate precipitation; HPLC; ion exchange chromatography; affinity chromatography (including immunoaffinity chromatography); and/or various size separations such as sedimentation, gel electrophoresis (SDS-PAGE), gel filtration or molecular sieve chromatography. All these methods are described above in detail.

High Performance Liquid Chromatography (HPLC) and FPLC are preferred methods since they provide very rapid separation with extraordinary resolution of peaks. Separation can be accomplished in a matter of minutes, or at most an hour and furthermore only a very small volume of the sample is needed. Also, the concentration of the sample need not be very great because the bands are so narrow that there is very little dilution of the sample. This is ideal for digested protein fragments.

M. Obtaining Nucleic Acid Sequences from Protein Sequences

The protein fragment sequences obtained above can then be used to obtain nucleic acid sequences by techniques well known to one of skill in the art. The techniques include artificial synthesis of nucleic acid polymers. Table 2 below describes the degeneracy of codons and provides the corresponding amino acid sequences. As known to the skilled artisan, one can use the codon preference or bias of an organism if known.

TABLE 2

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |

TABLE 2-continued

| Amino Acids | | | Codons |
|---|---|---|---|
| Tryptophan | Trp | W | UGG |
| Tyrosine | Tyr | Y | UAC UAU |

The nucleotides generated in the present invention include those encoding the isolated and purified proteins fragments as described above. It will also be understood that nucleic acid sequences (and their encoded amino acid sequences) may include additional residues, such as additional 5' or 3' sequences.

N. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

SAGE Tags. A group of SAGE tags 10 bases long were selected from the SAGE tag sequences database generated from epithelium cells of normal colon (Zhang et al., 1997). Each selected SAGE tag sequence was searched in the UniGene database to identify it as a matched or an unmatched tag sequence. Each matched sequence was given the appropriate Unigene ID number. Both matched and unmatched tags were used in the experiments.

RNA samples and cDNA synthesis. The same RNA sample from epithelium cells of normal human colon tissue was used for this experiment (Zhang et al., 1997). RNA samples from 24 different human tissues were also used for the detection of multiple expression (CloneTech). First strand cDNAs were generated through oligo-dT priming with a cDNA synthesis kit (Life Technologies), following the manufacturer's instruction. After cDNA synthesis, the excess free oligo-dT primers were removed using a MicroSpin S-300 column (Amersham Pharmacia).

PCR conditions. Pfu DNA polymerase (Stratagene) was used with 10× buffer (200 mM Tris-HCl pH 8.8, 100 mM KCl, 100 mM $(NH_4)_2SO_4$, 20 mM $MgSO_4$, 1% Triton X-100, 1 mg/ml BSA). Two mM $MgCl_2$ was added in each reaction to increase the $Mg^{++}$ concentration. The PCR mixture contained 1×buffer, 2 mM $MgCl_2$, 0.3 mM dNTPs, 0.04 unit/$\mu$l Pfu polymerase, 3 ng/$\mu$l sense primer, 1.5 ng/$\mu$l anchored oligo-dT primer (single or mixture) in final volume of 20 or 50 $\mu$l. The PCR reactions were performed first at 94° C. 1 min, followed by 5 cycles at 94° C. 20 sec, 50 to 53° C. 20 sec. 72° C. 20 sec. The conditions were then changed to 25 cycles at 94° C. 20 sec, 60° C. 20 sec, and 72° C. 20 sec. The reactions were kept at 72° C. for five minutes for the last cycle.

DNA cloning and sequencing. PCR amplified fragments were cloned into pCR-Blunt vector (InvitroGen). Positive clones were screened using PCR with M13 reverse and M13 forward (−20) primers located in the vector, or using EcoRI digestion. Plasmids were prepared with a plasmid purification kit (Qiagen). Sequencing reactions were performed with PE big-dye kit (PE Applied Biosystems) with M13 reverse primer, following the manufacturer's instruction.

Database search. All the sequences generated from the clones were searched using the BLAST program for alignment.

Example 2

Results and Discussion

The inventors envisioned that the amplification of a particular template corresponding to a particular SAGE tag will proceed as depicted in the schematic in FIG. 1, using a combination of a sense primer containing a SAGE tag sequence and a single-base anchored oligo-dT antisense primer. In this process, only the cDNA templates containing the binding sequences for the SAGE tag will be annealed and extended in the first PCR cycle. In the second cycle, the extension will only happen from that single-base anchored oligo-dT primer which anneals at the 5' end of the poly-dA sequences with the anchored-nucleotide correctly paired to the last nucleotide before the poly-dA sequence. Extension of all other anchored primers annealed along the poly-dA sequences will be blocked because of presence of the anchor nucleotide. The resulting extended templates will exclude poly-dA/dT sequences. Only the cDNA templates containing the SAGE tag sequence will undergo exponential amplification in the following PCR cycles. Thus, only copies of the same size will be generated.

Figure 2:
FIG. 2. Size distribution of NlaIII digested cDNA. Double strand cDNA was digested by NlaIII and electrophoresed on a 1.5% agarose gel to demonstrate the size distribution of the digested fragments.

The expected size distribution of amplified sequences using this strategy should be up to several hundred bases, because of the use of NlaIII digestion in the SAGE process for SAGE tag collection (Velculescu et al., 1995). NlaIII is a restriction enzyme recognizing CATG. As shown in FIG. 2, the size distribution of NlaIII digested cDNA was centered between 200 to 500 base pairs.

Design of primer. Each SAGE tag contains only a 10 base sequence. To increase the length of the primers for efficient PCR priming, CATG, a NlaIII recognition site used for collecting SAGE Tag fragments (Velculescu et al., 1995), was added 5' of the SAGE tag. A BamHI recognition site, GGATCC, was added 5' of the primer to increase the primer size and to provide a potential site for subcloning. For the anchored oligo-dT primers, a single-base anchor dA, dG, or dC was attached to the 3' end of the oligo-dT primer (Khan et al., 1991, Kiriangkum et al., 1992; Liang and Pardee, 1992, Liang et al., 1994; Wang and Rowley, 1998). To determine the best length of oligo-dT sequences, different numbers of dT nucleotides from 11 to 20 were tested, with dT11 giving the best results.

Optimizing PCR condition. Various PCR conditions were tested in order to maximize the specificity and efficiency of amplification. In the PCR reaction, the anchored primers were either combined separately with each sense primer, or a mixture of equal amounts of dA, dG and dC anchored primers was used with the sense primer. Pfu DNA polymerase was chosen for the PCR amplification because it showed greater fidelity of amplification compared with regular Taq DNA polymerase (Lundberg et al., 1991) (data not show). The $Mg^{++}$ concentration played an important role in determining the specificity and the yield of the PCR products. Satisfactory results were usually obtained at the final concentration of 4 mM $Mg^{++}$. The number of PCR cycles is important to maintain the specificity of the amplification. Over-amplification with a high number of PCR cycles could result in non-specific amplification.

Figure 3:
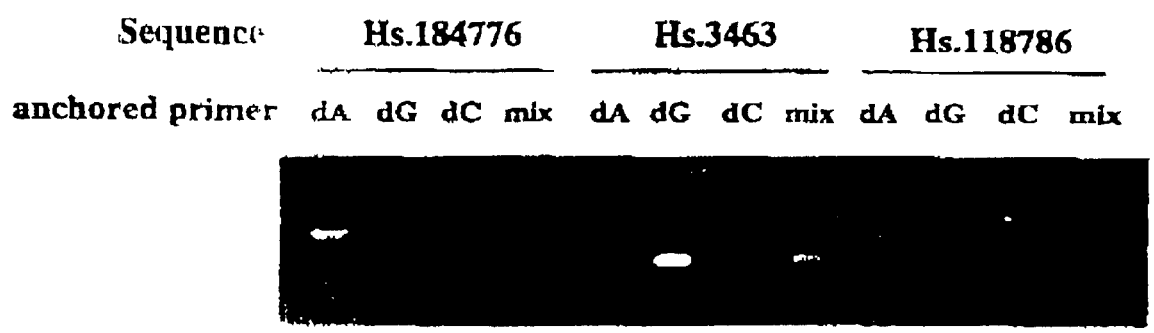
FIG. 3. Specific amplification of 3' sequences corresponding to a specific SAGE tag sequence by GLGI. In the PCR reaction, each SAGE tag sequence was used as the sense primer, each single dA, dG or dC or a mixture of three anchored oligo-dT primers was used as the antisense primers. The 3'-end nucleotide for Hs.184776 is dT, for Hs.3463 is dC, and for Hs.118786 is dG.

Amplification of longer sequences from SAGE tags. A group of SAGE tags generated from colon tissues was selected for the analysis (Zhang et al., 1997) (Table 3). PCR™ was performed with each sense primer containing the SAGE tag sequence and individual or mixed anchored oligo-dT primers, combined with cDNAs from colon tissue generated by oligo-dT priming. The PCR products were electrophoresed through an agarose gel, and cloned into vector for sequencing analysis. FIG. 3 shows examples of the PCR amplification with three SAGE tags that matched to known sequences. The last nucleotide before the poly-dA sequences for those three sequences (Hs.184776, Hs.3463 and Hs.118786) is dT, dC, and dG respectively. The inventors obtained the expected results. The amplification occurred only in the reaction with dA, dG and dC anchored oligo-dT for these three sequences. When the dA, dG and dC anchored oligo-dT primers were mixed for each reaction, the same amplification products can be generated even though the amplification efficiency was lower due to the competition of binding between these three primers. These data indicate that the reaction can be simplified into a single reaction using a combination of dA, dG and dC anchored oligo-dT primers. Table 3 summarizes the results generated from these experiments. For the matched SAGE tag sequences, amplification occurred when the correct anchor primers were used except for Hs.194659, which was amplified by dG anchored oligo-dT but the matched sequences ended with dT. The size distribution of these amplified fragments ranged from 77 to 382 base pairs. cDNA fragments were also generated from three unmatched SAGE tags, and they represent novel sequences.

Identify the correct sequence from multiple sequences that matched with the same SAGE Tag. When matching SAGE tag sequences in databases, a single SAGE tag may align with several sequences. For example, nine out of 40 SAGE tag sequences show matches to multiple Unigene Clusters (Zhang et al., 1997). Other than sharing the same SAGE tag sequence, these matched sequences have no homology and are derived from various different tissues. To test this issue experimentally, 12 SAGE tags were used for amplification with cDNA samples from 24 different human tissues. Four out of these 12 tags generated multiple templates. For example, the SAGE tag (GTCATCACCA) (SEQ ID NO: 17) generated five different sequences from five different tissues (fetal liver, skeletal muscle, spinal cord, trachea and colon), and two different sequences from the same tissue (spinal cord) (Table 4). All of these fragments contained the same SAGE tag sequence, but the rest of the sequences showed no homology. Among these sequences, the ones from colon tissue all matched the previous amplified sequences in the colon (Table 3). These data indicate that a SAGE tag itself may not be sufficient to serve as a unique identifier for a particular sequence, when several sequences share the same SAGE tag sequences. It is important to distinguish which one of the matched sequences is the correct sequence corresponding to the particular SAGE tag. To avoid the uncertainty when different sequences are expressed from different tissues, it will be necessary to generate the fragment from the same tissue used to generate the SAGE tag. The inventors' observations also indicate that relying only on a database search to identify the sequence corresponding to a SAGE tag may provide misleading information. Direct amplification of the specific template with the inventors strategy will be very useful for confirmation of the validity of a particular SAGE tag.

TABLE 3

Summary of GLGI results from SAGE Tags

| SAGE Tags (10 base) | Unigene ID | 3' end nucleotide in matched sequences* | Amplified by anchored oligo dT | Length of sequence (bs) | Match to original sequence** |
|---|---|---|---|---|---|
| GGAAGGTTTA (SEQ ID NO:18) | Hs.105484 | dT/dG | dT | 77 | + |
| AGATCCCAAG (SEQ ID NO:19) | Hs.50813 | dC/dG | dC | 84 | + |
| CTTATGGTCC (SEQ ID NO:20) | Hs.179608 | dT | dT | 86 | + |
| AGGATGGTCC (SEQ ID NO:21) | Hs.71779 | dC | dC | 112 | + |
| GTCATCACCA (SEQ ID NO:22) | Hs.32966 | dC | dC | 119 | + |
| GACCAGTGGC (SEQ ID NO:23) | Hs.143131 | dC/dT | dC | 135 | + |
| CTGTTGGTGA (SEQ ID NO:24) | Hs.3463 | dC | dC | 148 | + |
| ACTGGGTCTA (SEQ ID NO:25) | Hs.227823 | dG | dG | 150 | + |
| TACGGTGTGG (SEQ ID NO:26) | Hs.105460 | dC | dC | 166 | + |
| CGGTGGGACC (SEQ ID NO:27) | Hs.99175 | dC/dT/dG | dC | 200 | + |
| CCTTCAAATC (SEQ ID NO:28) | Hs.23118 | dC/dT | dC | 220 | + |
| GGAGGCGCTC (SEQ ID NO:29) | Hs.33455 | dT/dG | dT | 238 | + |
| AAGAAGATAG (SEQ ID NO:30) | Hs.73848 | dT | dT | 317 | + |
| GATCCCAACT (SEQ ID NO:31) | Hs.118786 | dG/dT/dC | dG | 329 | + |
| GAACAGCTCA (SEQ ID NO:32) | Hs.194659 | dT | dG | 382 | + |
| AGGTGACTGG (SEQ ID NO:33) | — | — | dC | 156 | — |
| CACCTAGTTG (SEQ ID NO:34) | — | — | dT | 170 | — |
| CCTGTCTGCC (SEQ ID NO:35) | — | — | dT | 249 | — |

*The 3' end nucleotides from all the sequences were included in each matched Unigene cluster.
**The amplified sequences were matched to databases again. The last three sequences have no matches and represent novel sequences.

Figure 4:
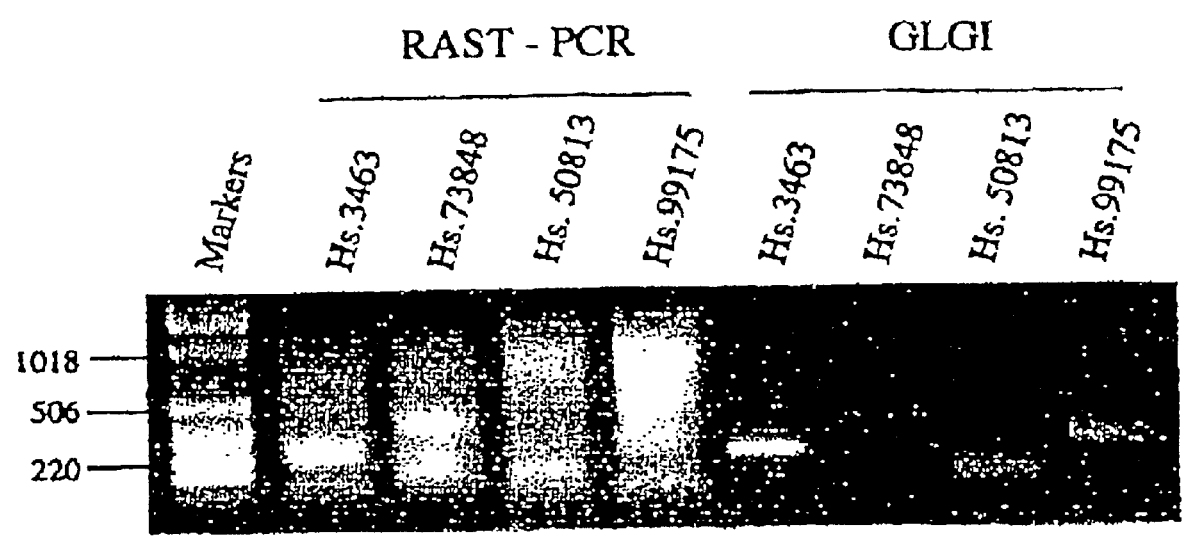
FIG. 4. Comparison between RAST-PCR method and GLGI method. A set of 4 SAGE tags was chosen for the analysis. The same RNA from human colon and sense primers were used for both methods. The conditions used for RAST-PCR followed the procedures described in reference (Van den Berg et al., 1999).

During the course of the research, the inventors became aware of a report describing a method RAST-PCR (Rapid RT-PCR Analysis of Unknown SAGE Tags) for analyzing unknown SAGE Tags (van den Berg et al., 1999). The authors used a sense primer that was designed based on a SAGE tag. However, the antisense primer was the M13 sequence tailed to 5' oligo-dT$_{24}$ used for cDNA synthesis. In the process of cDNA synthesis, oligo-dT primers anneal randomly along the poly-A sequences in the mRNA template. The resulting cDNAs include various lengths of poly-dA/dT sequences at the 3' of the cDNA, even from the same mRNA template. Using the M13 sequence tailed to the oligo-dT as the antisense primer for PCR will generate multiple fragments with different sizes or a smear due to the inclusion of different length of poly-dA sequences. Using the conditions described in that paper (Van den Berg, 1999), the inventors obtained the results the inventors expected, namely smears (FIG. 4).

TABLE 4

Detection of heterogeneous sequences in various
tissues containing the same SAGE Tag

| SAGE TAG | Positive tissues | Unigene ID | length of sequence |
|---|---|---|---|
| CGGTGGGACC (SEQ ID NO:14) | Colon, Thymus, Small intestine | Hs.99175 | 200 |
|  | Small intestine | no match | 368 |
|  | Thymus | no match | 90 |
| AGATCCCAAG (SEQ ID NO:15) | Colon, Heart, Placenta, Thymus | Hs.50813 | 84 |
|  | Placenta | no match | 53 |
|  | Skeletal muscle | Hs.85937 | 282 |
|  | Testis | no match | 227 |
|  | Thymus, Placenta | no match | 51 |
| CTTATGGTCC (SEQ ID NO:16) | Bone marrow | Hs.237416 | 393 |
|  | Bone marrow | no match | 144 |
|  | Colon | Hs.179608 | 86 |
| GTCATCACCA (SEQ ID NO:17) | Fetal liver, Spinal cord | Hs.222346 | 125 |
|  | Skeletal muscle | Hs.1288 | 399 |
|  | Spinal cord | Hs.9641 | 394 |
|  | Trachea | no match | 225 |
|  | colon | Hs.32966 | 136 |

The development of the GLGI method provides several potential applications. First, it provides a strategy for even wider application of the SAGE technique for quantitative analysis of global gene expression. Second, it can be used to identify the 3' cDNA sequence from any exon within a gene. These exons can include the ones predicted by bioinformatic tools. Third, a combined application of SAGE/GLGI can be applied to define the 3' boundary of expressed genes in the genomic sequences in human and in other eukaryotic genomes.

Example 3

High-throughput GLGI

A high-throughput GLGI procedure is also developed by the present inventors for converting a large set of SAGE tag sequences into gene identities.

Materials and Methods. SAGE tags were selected from the SAGE tag sequences generated from human and mouse myeloid cells, including 203 SAGE tags with multiple matches and 89 SAGE tags without matches. A set of 20 SAGE tags with a single match was used as controls to demonstrate the specificity of GLGI amplification.

The same RNA samples from human and mouse myeloid cells used for SAGE analysis were used as the templates for GLGI amplification. mRNAs from 5 µg of total RNA, of each sample were isolated with Oligo (dT)$_{25}$ Dynabeads (Dynal), following the manufacturer's protocol. Poly(dA/dT) cDNAs were synthesized using a cDNA synthesis kit (Cat. No: 18267-021, Life Technologies) and the 5' biotinylated, 3' anchored oligo (dT) primers were used for first strand cDNA synthesis (5' biotin-ATCTAGAGCGGCCGC-T16-A, G, CA, CG and CC) (SEQ ID NOS: 1–5) (Wang et al., 2000). The double-strand cDNAs were then digested with NlaIII, and 3' cDNAs were isolated with streptavidin beads (Dynal), following the manufactures protocol. In order to generate enough 3' cDNAs for GLGI analysis, 3' cDNA templates were amplified by PCR as the following: SAGE linker A or B was ligated to the 3' cDNAs bound to the beads (Linker A: 5'-TTTGGATTTGCTGGTGCAGTACAACTAGGCTT AATAGGGACATG-3' SEQ ID NO: 6 and 5'-$_p$TCCCTATTAAGCCTAGTTGTACTGCACCAGC AAATCC [amino mod. C7]-3' (SEQ ID NO: 7); or Linker B: 5'-TTTCTGCTCGAATTCAAGCTTCTAACGATGTA CGGGGA CATG -3' SEQ ID NO: 8 and 5'-$_p$TCCCCGTACATCGTTAGAAGGTTGAATTCG AGCAG [amino mod. 7]-3') (SEQ ID NO: 9). The ligated 3' cDNAs were then amplified by 20 cycles of PCR at 94° C. for 30 s, 55° C. for 30 s, and 72° C. for 30 s, with PLATINUM Taq polymerase (Life Technologies), SAGE sense primer (5'-GGATTTGCTGGTGCAG TACA-3' (SEQ ID NO: 10) for linker A; or 5'-CTGCTCGAATTCAAGCTTCT-3' (SEQ ID NO: 11 for linker B) and antisense primer (5'-ACTATCTAGAGCGGCCGCTT-3') (SEQ ID NO: 12) located in the 5' end of anchored oligo dT primers used for the first strand cDNA synthesis. The amplified templates were extracted by phenol/chloroform, precipitated by ethanol/NH$_4$OAc/glycogen, and resuspended in TE buffer for GLGI amplification.

The sense primer used for GLGI amplification included 14 base (CATG+10 base SAGE tag sequence) at the 3' end and 6 bases (GGATCC, BamH I sites) at the 5' of the primer, giving a total of 20 bases for each primer: 5'-GGATCCCATGNNNNNNNNNN-3' (SEQ ID NO: 13) (Chen et al., 2000). Sense primers were synthesized in 96 well format and the concentration was adjusted to 50 ng/µl with TE. GLGI master mixtures were prepared for each reaction, containing 1×PCR buffer (20 mM TrisCl pH 8.4, 50 mM KCl), 2 mM MgCl$_2$, 0.2 mM dNTPs, 1.5 units/0.3 µl PLATINUM Taq polymerase, 60 ng/1.2 µl antisense primer (5'-ACTATCTAGAGCGGCCGCTT-3') (SEQ ID NO: 12), and 0.5–5 ng of 3' cDNAs. The reaction mixtures were aliquoted into a 96-well plate at 28.8 µl per well. Sense primers (60 ng/1.2 µl) were then added into each well. GLGI reactions were performed in PB GeneAmp PCR Systems 9600 or 9700. The conditions used were 94° C. for 2 min, followed by five cycles at 94° C. for 30 s, 55° C. for 30 s, and 72° C. for 30 s. The conditions were then changed to 20–25 cycles at 94° C. for 30 s, 60° C. for 30 s, and 72° C. for 30 s. Reactions were kept at 72° C. for 5 min for the last cycle. The amplified products were directly precipitated in the 96-well PCR plate by adding 100 µl of precipitation mixture to each well, containing 1 µl of glycogen 20 mg/ml, Roche), 15 µl of 7.5M NH$_4$OAc and 84 µl of 100% ethanol. The plate was sea with Tape pads (QIAGEN, Inc), vortexed, and kept at room temperature for 15 mm. After spinning at 4000 rpm for 35 mm at 4° C. (SORVALL RC5C plus; rotor: SH3000), the supernatants were removed, 150 µl of 70% ethanol were added per well to wash the DNA, and the plate were spun at 4000 rpm for 15 minutes. The supernatants were removed again, the pallets were air-dried, and dissolved in 5 µl of dH$_2$O. Two µl of DNA, 0.7 µl of salt solution, 0.7 µl of water, and 6 ng of pCR4-TOPO vector were used for each ligation reaction with TOPO TA cloning kit for sequencing (Invitrogen). The ligation reactions were performed at room temperature for 25 min. For transformation, 2 µl of ligation were mixed with 50 µl of TOPO10 competent cells (Invitrogen), kept on ice for 20 min, then heated at 42° C. for 30 s, and moved on ice. SOC media (250 µl) were added per well. Plate was sealed, shaken at 37° C. for 60 mm at 225 rpm. The transformants were spread on LB plates containing 50 ng/ml of kanamycin and grew over night at 37° C. Positive clones were screened by direct colony-PCR. PCR master mixtures were prepared, containing 1×PCR buffer (10 mM TrisCl pH 8.3, 50 mM KCl, 1.5 mM MgCl$_2$), 0.1 mM dNTPs, 0.5 units/0.1 µl Taq polymerase (TaKaRa), 60 ng of sense prime (M13 reverse primer) and 60 ng of antisense primer (M13 forward (−20) primer). The reaction mixtures were aliquoted into a 96-well plate at 25 µl per well, and colonies were picked into the reaction mixtures with sterile pipette tips. PCR was performed in PE GeneAmp PCR Systems 9600 or 9700. The conditions used were 94° C. for 2 min, followed by 25 cycles at 94° C. for 30 s, 55° C. for 30 s, and 72° C. for 60 s. The reactions were kept at 72° C. for 5 min after the last cycle. 75 µl of precipitation mixture were added per well to precipitate DNAs, containing 22 µl of $dH_2O$, 15 µl of 2M $NaClO_4$ and 38 µl of 2-propanol. The plate was sealed, vortexed, and kept at room temperature for 5 min. After spinning at 4000 rpm for 35 min at 4° C., the supernatants were removed, 150 µl of 70% ethanol were added per well to wash the DNA, and the plate were spun at 4000 rpm for 25 minutes. Supernatants were removed again, the pallets were air-dried, and dissolved in 10 µl of $dH_2O$. Sequencing mixtures were prepared in a total volume of 7 µl, containing 0.8 µl of big-dye pre-mixture, 1.4 µl of dilution buffer (400mM TrisCl pH 9.0, 10 mM $MgCl_2$), 30 ng/0.3 µl of sequence primer (M13 reverse primer or M13 forward (−20) primer), 1.5 µl H2O, and 3 µl of DNA templates. Sequencing reactions were performed at 96° C. for 10 s, 50° C. for 5 s, and 60° C. for 4 min for 99 cycles. The final sequencing products were precipitated by adding 75 µl of precipitation mixture, consisting of 64 µl of 100% ethanol/3M NaOAc mixture (25:1), 1 µl of glycogen (20 mg/ml) and 10 µl $dH_2O$. The plate was sealed, vortexed, and kept at room temperature for 15 min. After spinning at 4000 rpm for 35 min at 4° C., the supernatants were removed, 150 µl of 70% ethanol were added per well to wash the DNA, and the plate were spun at 4000 rpm for 15 minutes. The supernatants were removed, the pallets were air-dried, and dissolved in 3 µl of loading dye. One µl was loaded in 5% sequencing gels. Four to six clones were sequenced for higher abundant SAGE tags, and 8 to 12 clones were sequenced for low abundant SAGE tags. Sequences were collected with an ABI 377 sequencer.

All collected sequences were matched to GenBank Database (NR and ESTs, through BLAST. Any mismatch between the SAGE tag sequence used for GLGI amplification and the SAGE tag sequence of the matched sequence in database was considered as non-specific amplification, and these sequences were eliminated from further analysis. The matched sequence ID was used to search UniGene database to obtain the UniGene cluster ID.

Figure 5:
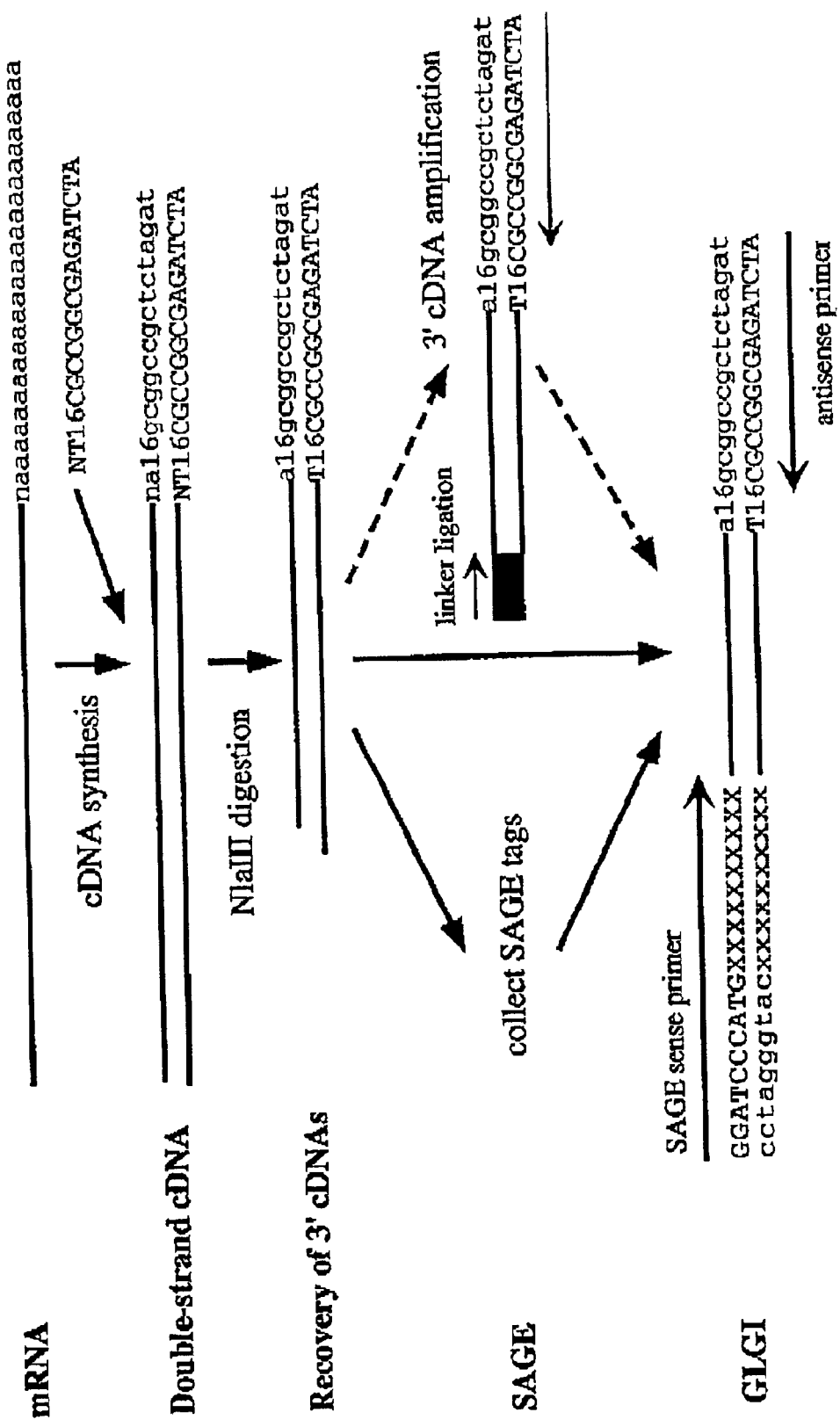
FIG. 5. Schematic for high-throughput GLGI.
Figure 6:
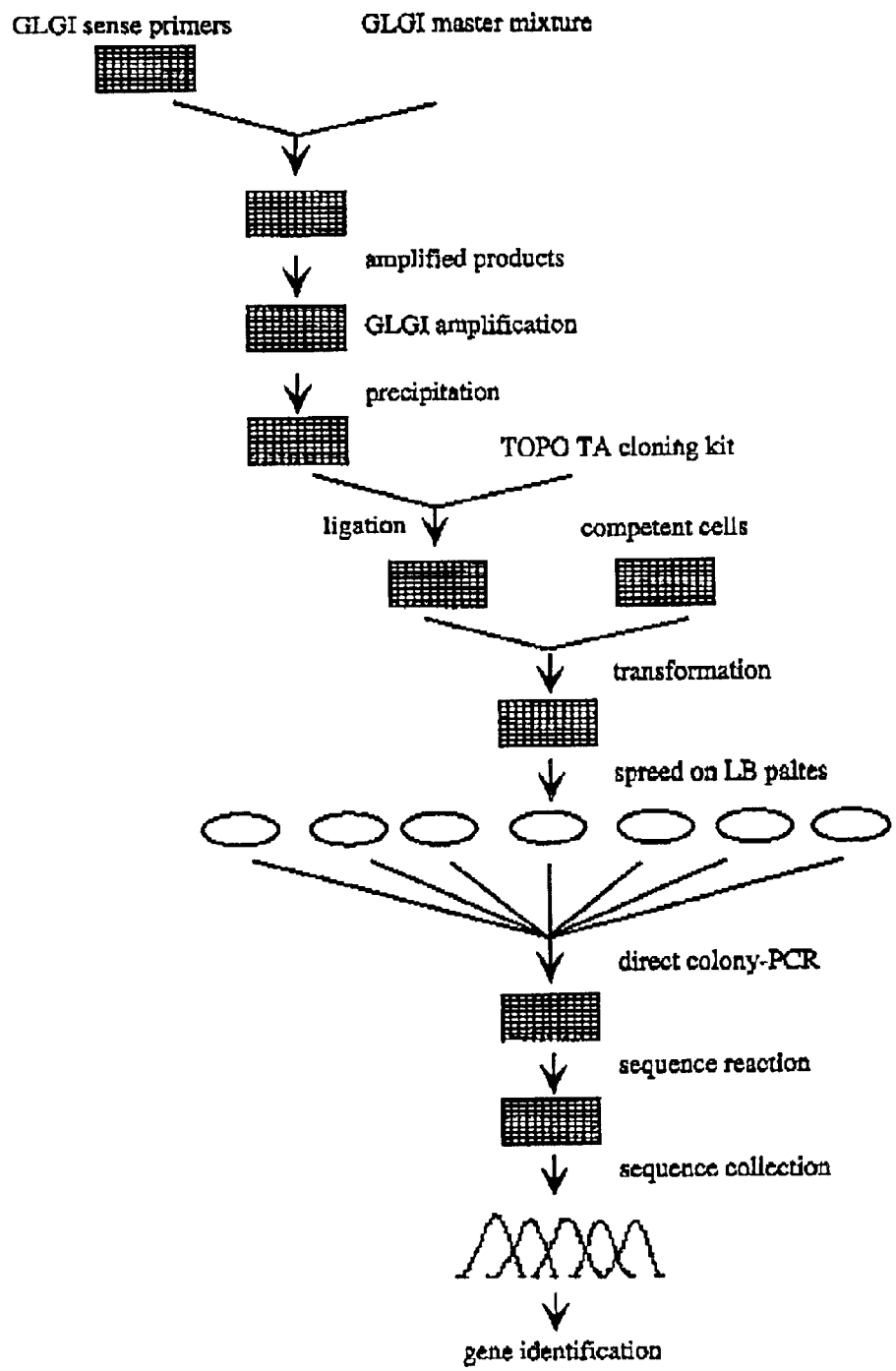
FIG. 6. Schematic for high-throughput GLGI amplification.

Results and Discussion. The details of the high-throughput GLGI method are outlined in FIG. 5 and FIG. 6. Double-strand poly(dA/dT)⁻ cDNAs are synthesized and digested with NlaIII. The 3' fragments are recovered with streptavidin-coated beads. Large quantity of 3' cDNAs templates can be generated by PCR amplifications of 3' cDNAs. GLGI amplification are performed. Then, 3' cDNA fragments corresponding to each specific SAGE tag are generated, cloned and sequenced. All the procedures are designed in 96 format to facilitate large-scale analyses. All the reagents used herein are optimized to guarantee the result and minimize expenses.

The high-throughput GLGI procedure has several differences as compared to the GLGI, for example, (i) 3' cDNAs instead of full-length cDNAs are used as the templates for GLGI amplification. This prevents artificial amplification from non-specific annealing of sense primer to sequences upstream of the last CATG. The 3' cDNAs can be amplified to provide sufficient templates for GLGI amplification; (ii) a single antisense primer (5'- ACTATCTAGAGCGGCCGCTT-3') (SEQ ID NO: 12) is used for all GLGI reactions instead of using combination of the five anchored oligo dT primers. The sequence of the antisense primer is located in 3' end of all the cDNA templates incorporated from anchored oligo dT primers used for the first strand cDNA synthesis. The inventors have observed that the anchored oligo dT primers are unstable which can hinder the successful performance of GLGI. Use of the single primer also increased the efficiency of GLGI amplification significantly as any annealing of this primer with 3' end sequence results in extension during PCR. In contrast, the use of five anchored oligo dT primers results in an extension by PCR only when correctly paired primers anneal. This feature is particularly useful to amplify the templates with low copies; (iii) PLATINUM Taq polymerase instead of Pfu DNA polymerase was used for GLGI amplification, in order to increase the yield of final products, while maintaining high specificity; (iv) the GLGI amplified DNAs were directly precipitated and cloned into vector without gel purification, to prevent the loss of amplified products. This is contemplated be particularly important for products with short sizes and for products generated from templates with low copies. The inventors data showed that these changes significantly increase efficiency and specificity for GLGI amplification of 3' cDNAs, especially for templates expressed at low level.

Figure 7:
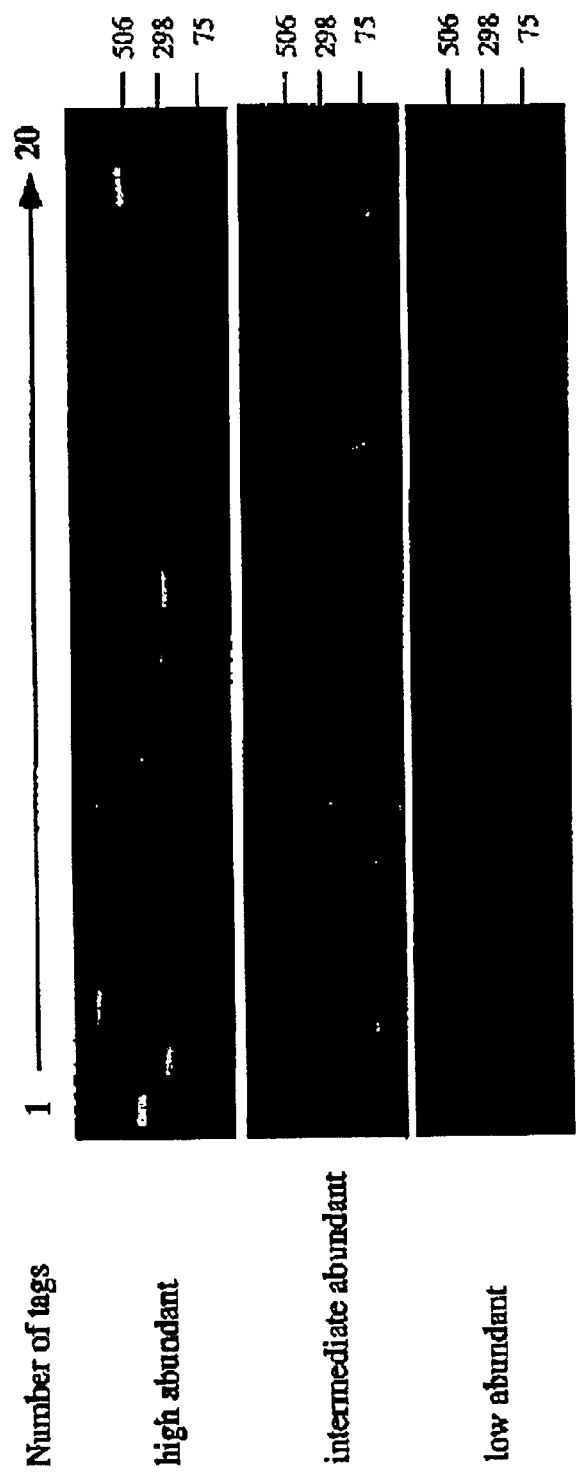
FIG. 7. Identification of correct 3' sequences for multiple matched SAGE tags. SAGE tags with multiple matches were selected from the high abundant, intermediate abundant and low abundant copies, and those tags were used as the sense primer for GLGI amplification. Gel demonstration of the 3' cDNAs amplified through GLGI.

The SAGE tags selected for the analysis herein include SAGE tags with single match, SAGE tags with multiple matches and SAGE tags without matches. FIG. 7 shows an example of the PCR amplifications. Table 5 summarizes these results. Nineteen out of 20 single-matched SAGE tag in the control reactions were converted into single 3' cDNA sequences and matched to the original matched single UniGene clusters. Seventy nine out of 89 unmatched novel SAGE tags were converted into longer 3' cDNA sequences proved by the presence of 3' poly dA/dT tail, no CATG site within the sequences, and no matches to known sequences. One hundred and eighty out of 203 of GLGI reactions from multiple matched SAGE tags generated 3' sequences, most of which (>90%), matched to a single UniGene cluster among the original multiple matched UniGene clusters. The efficiency for detection is parallel with the abundance of the SAGE tags. For higher abundant templates, the rate of success was nearly 100 percent. For the templates with low copies, the efficiency of detection was lower than that for high abundant SAGE tags. The inventors contemplate that this effect can be caused by low levels of template which reaches the limitation of the amplification.

TABLE 5

Summary of GLGI results.

| Number of Copy | SAGE tags | Number of matched UniGene clusters | GLGI identified genes |
|---|---|---|---|
| Over 50 | 6 | Single match | 6 |
|  | 150 | Multiple match | 136 |
|  | 3 | No match | 3 |
| 49 to 2 | 9 | Single match | 9 |
|  | 37 | Multiple match | 34 |
|  | 74 | No match | 68 |
| 1 | 5 | Single match | 4 |
|  | 16 | Multiple match | 10 |
|  | 12 | No match | 8 |
| Total | 312 |  | 278 |

Thus, the high-throughput GLGI procedure provides high efficiency for large-scale gene identification based on SAGE Tag sequences. By using this procedure, hundreds of interesting SAGE tags can be simultaneously converted into their 3' cDNA fragments. A large number of genes from genomes are expressed at low level, and these expressed genes can only be detected by SAGE technique. The combination of this GLGI procedure with large sets of SAGE tags detected from low copy templates provides an efficient way to identify these genes. Thus, this procedure will accelerate the completion of identification of expressed genes in the human genome as well as in other eukaryotic genomes.

All of the compositions and/or methods disclosed and claimed herein can be made and executed without undue experimentation in light of the present disclosure. While the compositions and method of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

Beaucage and Lyer, *Tetrahedron*, 48:2223–2311, 1992.
Bebenek and Kunkel, *Nucl. Acids Res.*, 17:5408, 1989.
Belkin and Jannasch, *Arch. Microbiol.*, 141:181–186, 1985.
Butler and Chamberlin, *J. Biol. Chem.*, 257:5772–5778, 1982.
Carr, Steven A., et al., "Mass Spectrometry in Bio-Pharmaceutical Research" in "Macro Molecular Sequencing and Synthesis Selected Methods and Applications", Publ. Alan R. Liss, Inc., pages 83–99, 1988
Chen J., Rowley J. D., Wang S. M., *Proc. Natl. Acad. Sci. USA.*, 97, 349–353, 2000.
Dale et al., *Plasmid*, 13:31–40, 1985.
D'Alessio and Gerard, *Nucl. Acids Res.*, 16:1999–2014, 1988.
Davanloo et al., *Proc. Nat'l Acad. Sci. USA*, 81:2035–2039, 1984.
Derbyshire et al., *Science*, 240:199–201, 1988.
Eckert and Kunkel, *PCR Methods and Applications*, 1:17–24, 1991.
Engler et al., *J. Biol. Chem.*, 258:11165–11173, 1983.
Gillam et al., *J. Biol. Chem.* 253, 2532, 1978.
Gillam et al., *Nucleic Acids Res.* 6, 2973, 1979.
Green et al., *Cell*, 32:681–694, 1983.
Gubler and Hoffmann, *Gene*, 25:263–269, 1983.
Gubler, *Methods Enzymol.*, 152:330–335, 1987.
Hashimoto, et al., *Blood*, 94:845–52, 1999.
Hibi, et al., *Cancer Res.*, 58:5690–5694, 1998.
Hori et al., *J. Biol. Chem.*, 254:11598–11604, 1979.
Houts et al., *J. Virol.*, 29:517–522, 1979.
http://www.sagenet.org/sage_protocol.htm
Hugh and Griffin, *PCR Technology*, 228–229, 1994.
Iiyy et al., *Biotechnique* 11:464, 1991.
Itakura and Riggs, *Science* 209:1401–1405, 1980.
Itakura et al., *J. Biol. Chem.* 250, 4592 1975
Khan, et al., *Nucleic Acids Res.*, 19:1715, 1991.
Khorana, *Science* 203, 614 1979
Kiriangkum, et al., *Nucleic Acids Res.*, 20:3793–3794, 1992.
Krieg and Melton, *Nucl. Acids Res.*, 12:7057–7070, 1984.
Kunkel et al., *Methods Enzymol.*, 154:367–382, 1987.
Lehman, *In: The Enzymes*, Boyer (Ed.), Vol. 14A, pp 16–38, Academic Press, San Diego, Calif., 1981.
Liang and Pardee, *Science*, 257:967–970, 1992.
Liang et al. *Nucleic Acids Res.* 22:5763–5764, 1994.
Liang, et al., *Nucleic Acids Res.*, 22:5763–5764, 1994.
Lundberg, et al., *Gene*, 108:1–6, 1991.
Madden, et al., *Oncogene*, 15:1079–1085, 1997.
Maniatis et al., *Cell*, 8:163, 1976.
Mattila et al., *NAR*, 19:4967–4973, 1991.
McClary et al., *J. DNA Sequencing Mapping*, 1(3):173–180, 1991.
Mead et al., *BioTechniques*, 11(1): 76–87, 1991.
Meinkoth and Wahl, *Methods Enzymol.*, 152:91–94, 1987.
Melton, *Proc. Nat'l Acad. Sci. USA*, 82:144–148, 1985.
Murray and Kelley, *Molec. Gen. Genet.*, 175:77–87, 1979.
Nordstrom et al., *J. Biol. Chem.*, 256:3112–3117, 1981.
Noren, *Nucl. Acids Res.*, 18:83–88, 1990.
Perler et al, *Proc Nat'l Acad Sci. USA*, 89(12):5577–81, 1992.
Sambrook et al., *In: Molecular Cloning: A Laboratory Manual*, second edition, Cold Spring Harbor Laboratory, Cold Spring Harbor, N.Y., 1989.
Sanger et al., *Proc. Nat'l Acad. Sci. USA*, 74:5463–5467, 1977.
Schenborn and Meirendorf, *Nucl. Acids Res.*, 13:6223–6236, 1985.
Studier et al., *Methods Enzymol.*, 185:60–89, 1990.
Tabor and Struhl, *In: Current Protocols in Molecular Biology*, Ausubel et al. (Eds.), John Wiley and Sons, NY, pp 3.5.10–3.5.12, 1989.
Tanese and Goff, *Proc. Nat'l Acad. Sci. USA*, 85:1977, 1988.
U.S. Pat. No. 4,704,362
U.S. Pat. No. 5,221,619
U.S. Pat. No. 5,583,013
U.S. Pat. No. 5,968,743
U.S. Pat. No. 4,659,774
U.S. Pat. No. 4,683,195,
U.S. Pat. No. 4,683,202
U.S. Pat. No. 4,800,159,
U.S. Pat. No. 4,816,571
U.S. Pat. No. 4,883,750
U.S. Pat. No. 4,959,463
U.S. Pat. No. 5,141,813
U.S. Pat. No. 5,207,880
U.S. Pat. No. 5,262,311
U.S. Pat. No. 5,264,566
U.S. Pat. No. 5,308,751
U.S. Pat. No. 5,360,523
U.S. Pat. No. 5,405,746
U.S. Pat. No. 5,428,148
U.S. Pat. No. 5,432,065
U.S. Pat. No. 5,455,008
U.S. Pat. No. 5,523,206
U.S. Pat. No. 5,554,744
U.S. Pat. No. 5,574,146
U.S. Pat. No. 5,602,244
U.S. Pat. No. 5,608,063
U.S. Pat. No. 5,639,608
U.S. Pat. No. 5,665,547
U.S. Pat. No. 5,674,716
U.S. Pat. No. 5,755,943
U.S. Pat. No. 5,780,232
U.S. Pat. No. 5,817,797
U.S. Pat. No. 5,821,058

U.S. Pat. No. 5,821,060
U.S. Pat. No. 5,846,727
U.S. Pat. No. 5,858,671
U.S. Pat. No. 5,866,330
U.S. Pat. No. 5,985,556
U.S. Pat. No. 6,004,446
U.S. Pat. No. 5,866,328
U.S. Pat. No. 5,876,934
Van den Berg, et al., *Nucleic Acids Res.*, 27:e17, 1999.
Velculescu, et al., *Cell*, 88:243–251, 1997.
Velculescu, et al., *Science*, 270:484–487, 1995.
Velculescu, et al., *Nat Genet.* 23:387–8, 1999.
Wang and Rowley, *Proc. Nat'l Acad. Sci. USA*, 95:11909–11914, 1998.
Wang, S. M., Fears, S. C., L. Zhang, J. J. Chen, J. D. Rowley, *Proc Natl Acad Sci USA*. 97, 4162, 2000.
WO 90/07641, filed Dec. 21, 1990.
Zhang, et al., *Science*, 276:1268–1272, 1997.
Zinn et al., *Cell*, 34:865–879, 1983.

What is claimed is:

1. A method for characterizing a SAGE tag fragment comprising:
   a) obtaining a RNA sample from the same tissue type as used in generating said SAGE tag;
   b) generating a cDNA fragment-comprising the sequence of the SAGE tag from said RNA sample by performing a DNA amplification reaction wherein primers used comprise:
      (i) a SAGE tag sequence as a sense primer; and
      (ii) at least one single-base anchored oligo-dT prime as an antisense primer; and
   c) analyzing said cDNA fragments.

2. The method of claim 1, wherein said RNA sample is the RNA sample used to perform SAGE.

3. The method of claim 1, wherein said DNA amplification comprises a polymerase chain reaction.

4. The method of claim 3, wherein the DNA polymerase used for said polymerase chain reaction is Pfu DNA polymerase.

5. The method of claim 3, comprising a $Mg^{2+}$ concentration of 4 mM.

6. The method of claim 1, wherein said cDNA fragment generated is about 50 to 600 base pairs in length.

7. The method of claim 1, wherein said single-base anchored oligo-dT primer comprises a single-base anchored to the 3' end of the oligo-dT primer, said single base excluding dT.

8. The method of claim 1, wherein said single-base anchored oligo-dT primer comprises from 10 to 25 poly-dT residues.

9. The method of claim 8, wherein said single-base anchored oligo-dT primer comprises 11 poly-dT residues.

10. The method of claim 1, wherein said sense primer further comprises a BamHI recognition sequence at the 5' end.

11. The method of claim 1, wherein said SAGE tag further comprises a NlaIII recognition sequence at the 5' end.

12. The method of claim 1, wherein said analyzing comprises:
    i) cloning said cDNA fragment; and
    ii) sequencing said clone to identify said cDNA fragment sequence.

13. The method of claim 12, further comprising comparing the cDNA sequence to known sequences.

14. The method of claim 1, wherein said analyzing comprises hybridizing the cDNA fragments with a known sequence.

15. The method of claim 1, wherein said analyzing comprises cloning a full-length cDNA.

16. The method of claim 1, wherein said analyzing comprises performing a DNA amplification reaction comprising:
    i) a sense primer designed based on an existing exon sequence; and
    ii) a single-base anchored oligo-dT primer as an antisense primer, thereby generating an amplified DNA; and further comprising
    iii) cloning and sequencing the amplified DNA.

17. The method of claim 16, wherein the exon sequences are predicted by a bioinformatics tool.

18. The method of claim 17, further comprising aligning the sequence of the amplified cDNA with a genomic DNA sequence.

19. The method of claim 1, wherein the tissue type is selected from the group consisting of colon, thymus, small intestine, heart, placenta, skeletal muscle, testes, bone marrow, trachea, spinal cord, liver, spleen, brain, lung, ovary, prostate, skin, cornea, retina, and breast.

20. The method of claim 15, wherein the full length cDNA is cloned into an expression vector.

* * * * *

UNITED STATES PATENT AND TRADEMARK OFFICE
CERTIFICATE OF CORRECTION

| | |
|---|---|
| PATENT NO. | : 6,916,610 B2 |
| APPLICATION NO. | : 09/748,710 |
| DATED | : July 12, 2005 |
| INVENTOR(S) | : San Ming Wang, Jian-jun Chen and Janet D. Rowley |

It is certified that error appears in the above-identified patent and that said Letters Patent is hereby corrected as shown below:

Please insert at column 1, line 10:

--Government Interests

The U.S. Government owns rights in the invention pursuant to National Institute of Health grant numbers CA 042557 and CA 078862.--

Signed and Sealed this

Fifth Day of February, 2008

JON W. DUDAS
*Director of the United States Patent and Trademark Office*

```
                      SEQUENCE LISTING

<160> NUMBER OF SEQ ID NOS: 35

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
atctagagcg gccgctttttt ttttttttttt ta                                    32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
atctagagcg gccgctttttt ttttttttttt tg                                    32

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
atctagagcg gccgctttttt ttttttttttt tca                                   33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4
atctagagcg gccgctttttt ttttttttttt tcg                                   33

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:  Synthetic
      Primer
```

```
<400> SEQUENCE: 5
atctagagcg gccgctttt tttttttttt tcc                               33

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
tttggatttg ctggtgcagt acaactaggc ttaataggga catg                  44

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
tccctattaa gcctagttgt actgcaccag caaatcc                          37

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
tttctgctcg aattcaagct tctaacgatg tacggggaca tg                    42

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
tccccgtaca tcgttagaag cttgaattcg agcag                            35

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
ggatttgctg gtgcagtaca                                             20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
```

-continued

```
ctgctcgaat tcaagcttct                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
actatctaga gcggccgctt                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (11)..(20)
<223> OTHER INFORMATION: N = A, T/U, C or G

<400> SEQUENCE: 13
ggatcccatg nnnnnnnnnn                                              20

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
cggtgggacc                                                         10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
agatcccaag                                                         10

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
cttatggtcc                                                         10

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
```

```
                          Primer

<400> SEQUENCE: 17
gtcatcacca                                                         10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
ggaaggttta                                                         10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
agatcccaag                                                         10

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
cttatggtcc                                                         10

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
aggatggtcc                                                         10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
gtcatcacca                                                         10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer
```

<400> SEQUENCE: 23
gaccagtggc                                                                    10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
ctgttggtga                                                                    10

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
actgggtcta                                                                    10

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
tacggtgtgg                                                                    10

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
cggtgggacc                                                                    10

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
ccttcaaatc                                                                    10

<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 29
ggaggcgctc                                                          10

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
aagaagatag                                                          10

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
gatcccaact                                                          10

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
gaacagctca                                                          10

<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
aggtgactgg                                                          10

<210> SEQ ID NO 34
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
cacctagttg                                                          10

<210> SEQ ID NO 35
<211> LENGTH: 10
<212> TYPE: DNA
<213> ORGANISM: Artificial Sequence
<220> FEATURE:
```

```
-continued

<223> OTHER INFORMATION: Description of Artificial Sequence:  Synthetic
      Primer

<400> SEQUENCE: 35
cctgtctgcc                                                                          10
```